(12) United States Patent
Gushurst et al.

(10) Patent No.: US 9,546,183 B2
(45) Date of Patent: *Jan. 17, 2017

(54) FORMS OF RIFAXIMIN AND USES THEREOF

(71) Applicant: Salix Pharmaceuticals, Ltd, Raleigh, NC (US)

(72) Inventors: Karen S. Gushurst, West Lafayette, IN (US); Donglai Yang, Annandale, NJ (US); Petinka Vlahova, West Lafayette, IN (US); Jeffrey S. Stults, Lafayette, IN (US)

(73) Assignee: Salix Pharmaceuticals, Ltd, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/995,791

(22) Filed: Jan. 14, 2016

(65) Prior Publication Data

US 2016/0200738 A1    Jul. 14, 2016

Related U.S. Application Data

(63) Continuation of application No. 14/062,333, filed on Oct. 24, 2013, now Pat. No. 9,273,066, which is a continuation of application No. 13/587,537, filed on Aug. 16, 2012, now Pat. No. 8,569,326, which is a continuation of application No. PCT/US2011/024981, filed on Feb. 16, 2011, which is a continuation of application No. 12/708,836, filed on Feb. 19, 2010, now Pat. No. 8,486,956, which is a continuation-in-part of application No. 12/393,012, filed on Feb. 25, 2009, now Pat. No. 8,067,429.

(60) Provisional application No. 61/031,329, filed on Feb. 25, 2008.

(51) Int. Cl.
*C07D 498/22* (2006.01)
*C07D 498/12* (2006.01)

(52) U.S. Cl.
CPC ........... *C07D 498/22* (2013.01); *C07D 498/12* (2013.01)

(58) Field of Classification Search
CPC .................................................. C07D 498/22
See application file for complete search history.

(56) References Cited

U.S. PATENT DOCUMENTS

| | | |
|---|---|---|
| 4,341,785 A | 7/1982 | Marchi et al. |
| 4,557,866 A | 12/1985 | Cannata et al. |
| 7,045,620 B2 | 5/2006 | Viscomi et al. |
| 7,612,199 B2 | 11/2009 | Viscomi et al. |
| 7,709,634 B2 | 5/2010 | Kothakonda et al. |
| 7,906,542 B2 | 3/2011 | Viscomi et al. |
| 7,915,275 B2 | 3/2011 | Viscomi et al. |
| 8,067,429 B2 | 11/2011 | Gushurst et al. |
| 8,486,956 B2 | 7/2013 | Gushurst et al. |
| 8,569,326 B2 | 10/2013 | Gushurst et al. |
| 8,754,098 B2 | 6/2014 | Gushurst et al. |
| 2005/0272754 A1 | 12/2005 | Viscomi et al. |
| 2006/0019986 A1 | 1/2006 | Ding et al. |
| 2006/0210592 A1 | 9/2006 | Kodsi |
| 2008/0132530 A1 | 6/2008 | Viscomi et al. |
| 2008/0262012 A1 | 10/2008 | Viscomi et al. |
| 2008/0262024 A1 | 10/2008 | Viscomi et al. |
| 2008/0262220 A1 | 10/2008 | Viscomi et al. |
| 2008/0262232 A1 | 10/2008 | Viscomi et al. |
| 2009/0011020 A1 | 1/2009 | Viscomi et al. |
| 2009/0082558 A1 | 3/2009 | Kothakonda et al. |
| 2009/0130201 A1 | 5/2009 | Viscomi et al. |
| 2009/0312357 A1 | 12/2009 | Rao et al. |
| 2009/0324736 A1 | 12/2009 | Johnson et al. |
| 2010/0136125 A1 | 6/2010 | Jacobus et al. |
| 2010/0174064 A1 | 7/2010 | Gushurst et al. |
| 2011/0086871 A1 | 4/2011 | Viscomi et al. |
| 2012/0035202 A1 | 2/2012 | Viscomi et al. |
| 2012/0289532 A1 | 11/2012 | Lavagna et al. |

FOREIGN PATENT DOCUMENTS

| | | |
|---|---|---|
| CN | 1886408 | 12/2006 |
| CN | 1886408 A | 12/2006 |
| CN | 1900077 A | 1/2007 |
| CN | 101031572 | 9/2007 |
| CN | 101031572 A | 9/2007 |
| EP | 0161534 A2 | 11/1985 |
| EP | 1557421 A1 | 7/2005 |
| EP | 1698630 A1 | 9/2006 |
| EP | 2257557 A2 | 12/2010 |
| IT | MI2005A000345 | 3/2005 |
| JP | 2003519698 A | 6/2003 |
| JP | 2005139161 A | 6/2005 |
| JP | 2007509904 A | 4/2007 |
| RU | 2403015 C2 | 11/2010 |
| WO | 01/51919 A2 | 7/2001 |
| WO | 2005044823 A2 | 5/2005 |
| WO | 2006/094737 A2 | 9/2006 |

(Continued)

OTHER PUBLICATIONS

Brufani, M. et al., "X-Ray Crystal Structure of 4-Deoxy-3'-bromopyrido[1,2'-1,2]imidazo[5,4-c]rifamycin S," The Journal of Antibiotics, 37:12, 1623-1627 (Dec. 1984).

Database CA [Online] Chemical Abstracts Service, Columbus, Ohio, US; Marcon, Giuliano: "Crystalline form of rifaximin and method of preparation" XP002637581, retrieved from STN Database accesion No. 2009:1314795 & IT 200 5MI 034 A1 (SOLMAG S. P.A., Italy) May 18, 2011 (May 18, 2011).

(Continued)

*Primary Examiner* — Bruck Kifle

(74) *Attorney, Agent, or Firm* — McCarter & English, LLP; Jonathan M. Sparks; Michael J. DeGrazia

(57) ABSTRACT

The present invention relates to Rifaximin polymorphic forms, to their use in medicinal preparations and to therapeutic methods using them.

4 Claims, 23 Drawing Sheets

(56) References Cited

FOREIGN PATENT DOCUMENTS

| WO | 2006094662 A1 | 9/2006 |
| WO | 2006094737 A2 | 9/2006 |
| WO | 2008035109 A1 | 3/2008 |
| WO | 2008155728 A1 | 12/2008 |
| WO | 2009008005 A1 | 1/2009 |
| WO | 2009047801 A1 | 4/2009 |
| WO | 2009108730 A2 | 9/2009 |
| WO | 2010033179 A1 | 3/2010 |
| WO | 2010067072 A1 | 6/2010 |
| WO | 2011051971 A2 | 5/2011 |
| WO | 2011/103120 A1 | 8/2011 |
| WO | 2011/153444 A1 | 12/2011 |
| WO | 2011/156897 A2 | 12/2011 |
| WO | 2012/109605 A2 | 8/2012 |

OTHER PUBLICATIONS

Italian Product Label for Normix (rifaximin), Apr. 23, 1985.
Rossi, C. et al., "NMR Investigation of a New Semisynthetic Bioactive Compound," Bulletin of Magnetic Resonance, 1996, vol. 18, No. 1-2, pp. 87-90.
US Package Insert for XIFAXAN (rifaximin) Mar. 2008.
Viscomi, G. et al., "Crystal Forms of Rifaximin and Their Effect on Pharmaceutical Properties," CrystEngComm, 2008, 10, 1074-1081.
Brufani, M. et al., "X-Ray Crystal Structure of 4-Deoxy-3'-bromopyrido[1,2'-1,2]imidazo[5,4-c]rifamycin S," The Journal of Antibiotics, 37(12):1623-1627 (Dec. 1984).
Giuliano et al., "Crystalline form of rifaximin and method of preparation", XP002637581, Abstract only, (2005).
Do Not Cite—Giuliano et al., "Crystalline form of rifaximin and method of preparation", XP002637581, Abstract, (2005).
Database CA [Online] Chemical Abstracts Service, Columbus, Ohio, US; Viscomi, Guiseppe Claudio et al, "New polymorphous forms of rifaximin for pharmaceuticals" XP002696258, Jun. 11, 2012 (Jun. 11, 2012).
Vippagunta, et al., "Crystalline Solids," Advanced Drug Delivery Reviews, vol. 48, Rev. 3, 2001, pp. 3-26.
Yusaku Shioji, Manufacturing Technology of Solid Formulation, CMC Publishing, Jan. 27, 2003, Trade Edition, the 9th, pp. 12-13.
Kazuhide Settsu, Chemistry of Drug Polytypism and Crystallization, 2002, p. 273, 278, 305-17.

Dynamic vapor sorption/desorption of rifaximin Form Iota

| | | |
|---|---|---|
| Max Equil Time | 180 min | |
| Equil Crit | 0.0100 wt % in | 5.00 min |
| T-RH Steps | 25, 5; 25, 15; 25, 25; 25, 35; 25, 45; 25, 55; 25, 65; 25, 75; 25, 85; 25, 95; 25, 85; 25, 75; 25, 65; 25, 55; 25, 45; 25, 35; 25, 25; 25, 15; 25, 5 | |
| Data Logging Interval | 2.00 min or | 0.0100 wt % |
| Expt Started | 1/23/2009 | |
| Run Started | 6:13:26 | |

| Elap Time min | Weight mg | Weight % chg | Samp Temp deg C | Samp RH % |
|---|---|---|---|---|
| 0.1 | 7.748 | 0.000 | 24.75 | 126.87 |
| 152.6 | 7.588 | -2.064 | 25.35 | 5.02 |
| 177.2 | 7.676 | -0.921 | 25.36 | 14.92 |
| 207.9 | 7.745 | -0.038 | 25.37 | 24.88 |
| 234.1 | 7.802 | 0.697 | 25.37 | 34.85 |
| 267.4 | 7.854 | 1.366 | 25.36 | 44.84 |
| 301.1 | 7.903 | 1.998 | 25.37 | 55.08 |
| 334.8 | 7.946 | 2.558 | 25.37 | 64.80 |
| 375.0 | 7.990 | 3.124 | 25.34 | 74.57 |
| 424.3 | 8.035 | 3.708 | 25.31 | 84.57 |
| 524.3 | 8.097 | 4.503 | 25.31 | 94.57 |
| 554.4 | 8.068 | 4.137 | 25.30 | 85.42 |
| 586.5 | 8.032 | 3.667 | 25.30 | 75.37 |
| 643.8 | 7.986 | 3.079 | 25.29 | 65.01 |
| 709.6 | 7.937 | 2.443 | 25.29 | 55.05 |
| 764.7 | 7.883 | 1.745 | 25.28 | 45.05 |
| 813.6 | 7.824 | 0.984 | 25.28 | 35.07 |
| 854.2 | 7.759 | 0.140 | 25.27 | 25.10 |
| 889.8 | 7.685 | -0.814 | 25.27 | 15.21 |
| 950.5 | 7.578 | -2.190 | 25.27 | 4.98 |

FIG. 11

FIG. 14
Hot stage images for rifaximin, Form ι
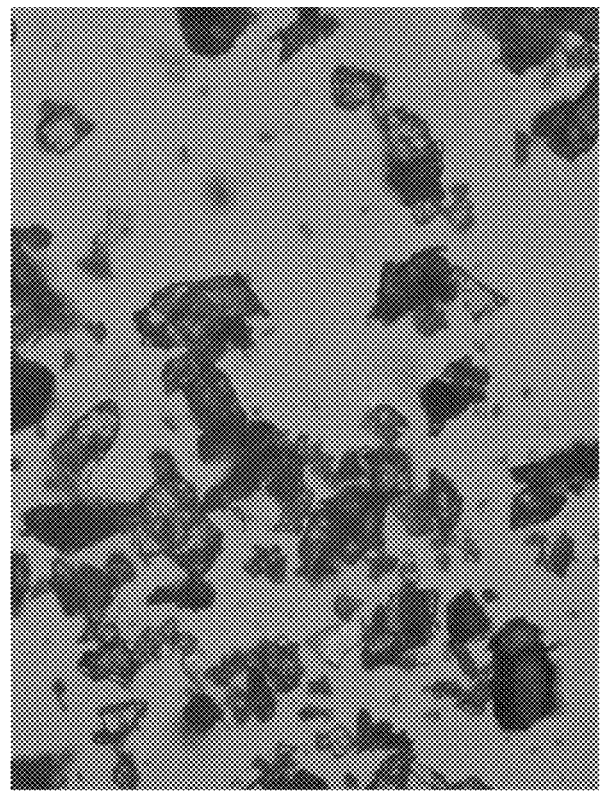
T = 30 °C, with no top polarizer
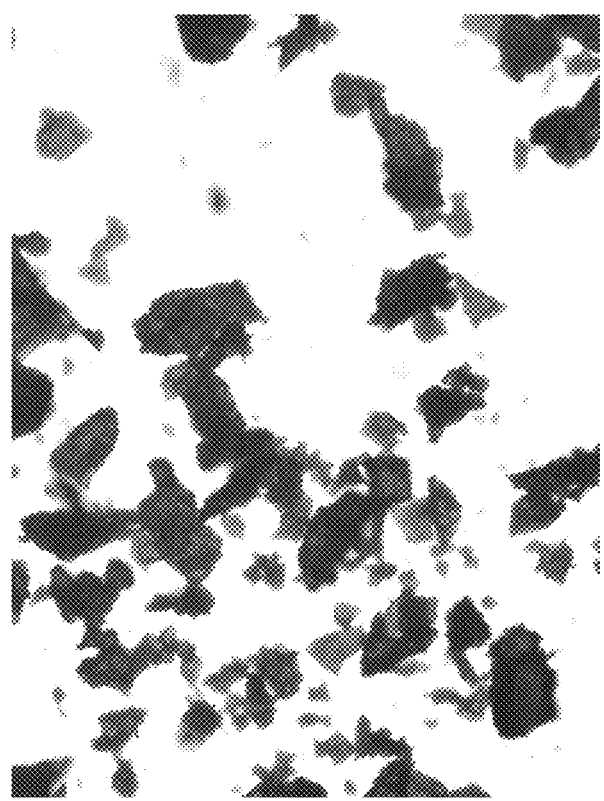
T = 30 °C, no top polarizer

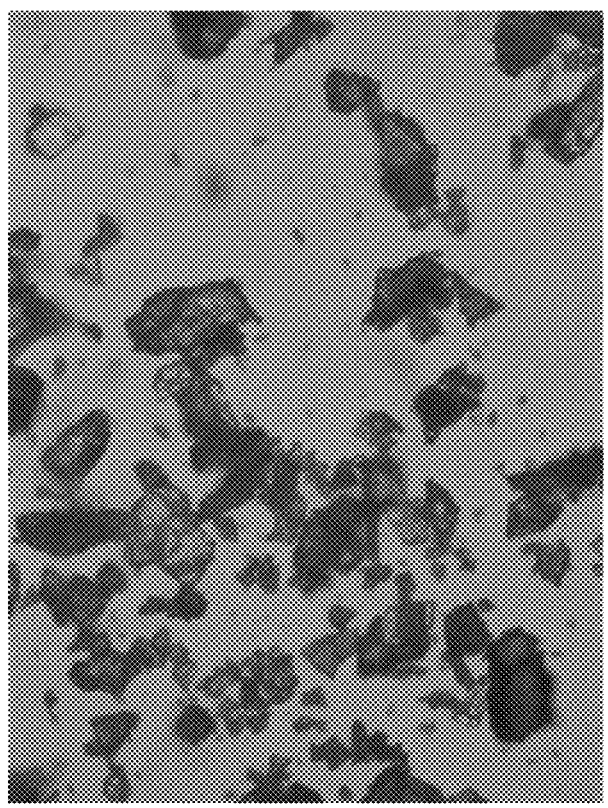
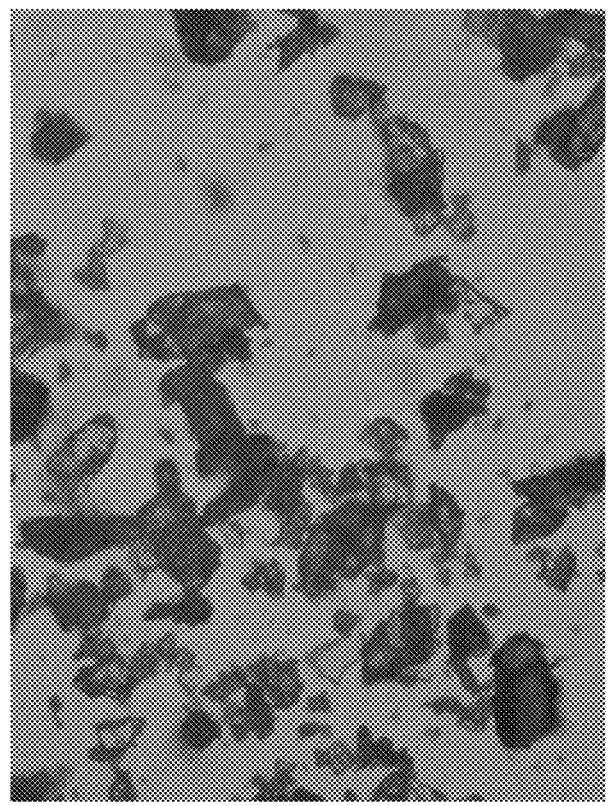
FIG. 14 (continued)
Hot stage images for rifaximin, Form ι

FIG. 14 (continued)
Hot stage images for rifaximin, Form ι
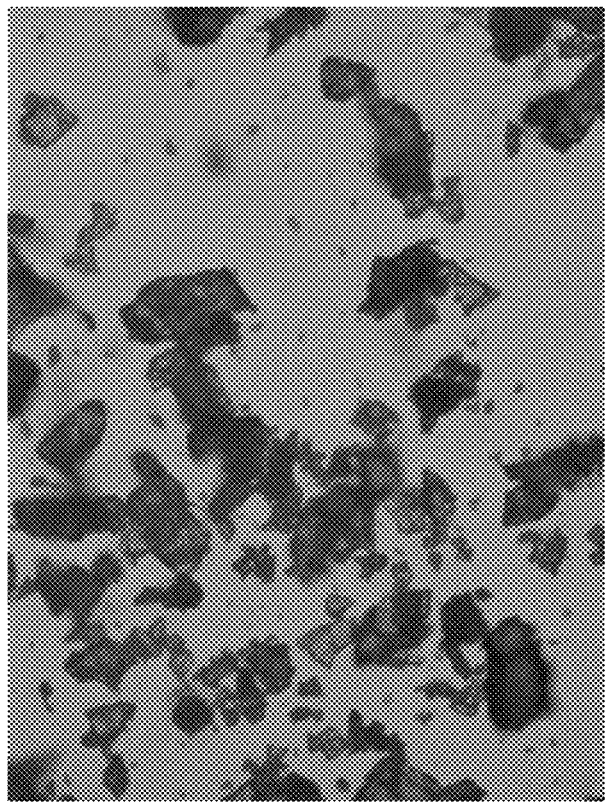
T = 204 °C
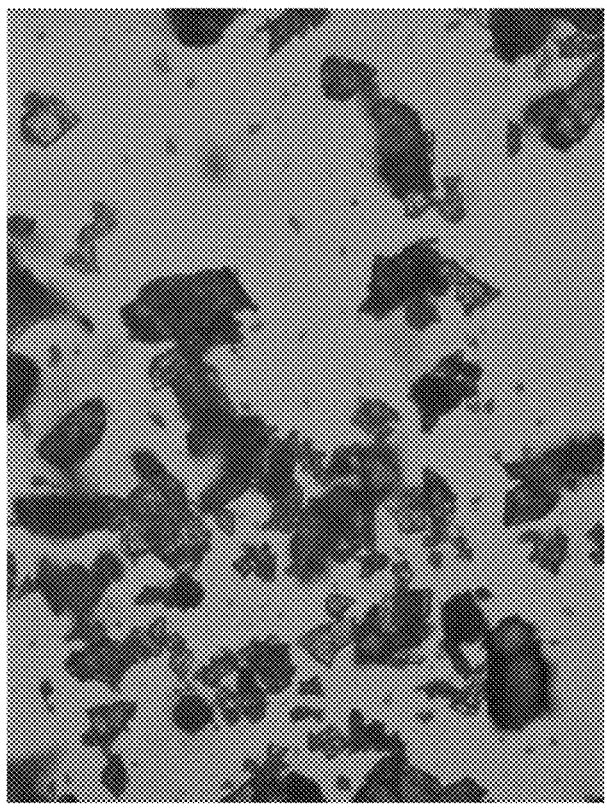
T = 190 °C

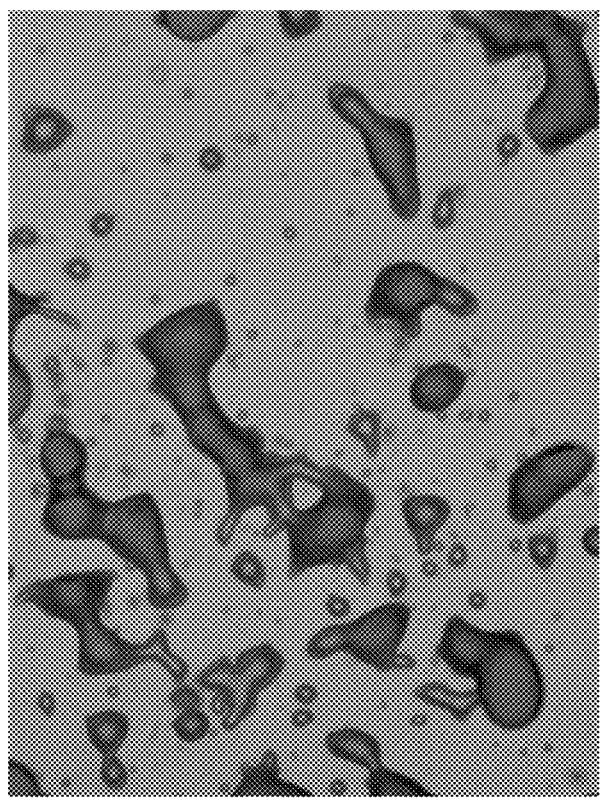
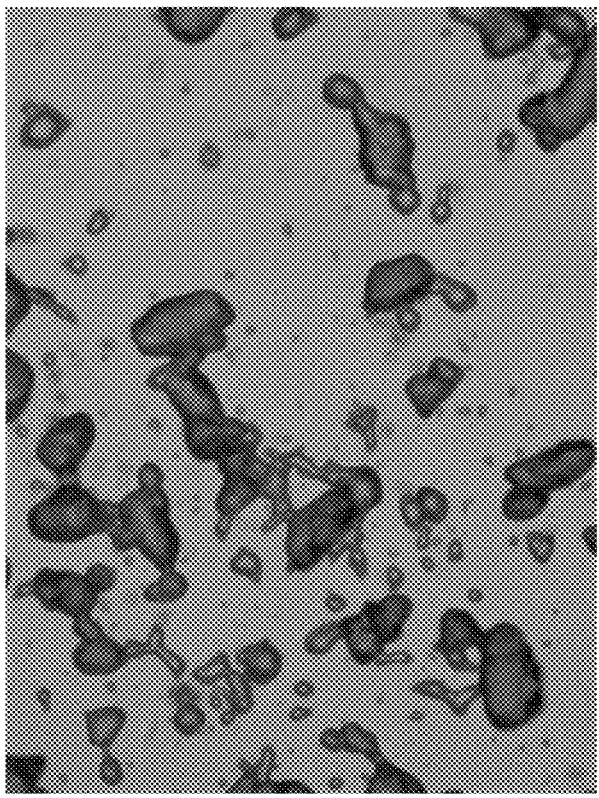
FIG. 14 (continued)
Hot stage images for rifaximin, Form ι
T = 222 °C
T = 218 °C Hot stage images for rifaximin, Form τ

T = 250 °C

FORMS OF RIFAXIMIN AND USES THEREOF

RELATED APPLICATIONS

This application is a continuation of U.S. application Ser. No. 14/062,333, filed Oct. 24, 2013, now U.S. Pat. No. 9,273,066, which is a continuation of U.S. application Ser. No. 13/587,537, filed Aug. 16, 2012, now U.S. Pat. No. 8,569,326, which is a continuation of PCT/US2011/024981, filed Feb. 16, 2011, which is a continuation of U.S. application Ser. No. 12/708,836, filed Feb. 19, 2010, now U.S. Pat. No. 8,486,956, which is a continuation-in-part of U.S. application Ser. No. 12/393,012, filed Feb. 25, 2009, now U.S. Pat. No. 8,067,429, which claims the benefit of U.S. Provisional Application No. 61/031,329, filed Feb. 25, 2008. The entire contents of each of the aforementioned applications are hereby expressly incorporated herein by reference.

BACKGROUND

Rifaximin (INN; see The Merck Index, XIII Ed., 8304) is an antibiotic belonging to the rifamycin class of antibiotics, e.g., a pyrido-imidazo rifamycin. Rifaximin exerts its broad antibacterial activity, for example, in the gastrointestinal tract against localized gastrointestinal bacteria that cause infectious diarrhea, irritable bowel syndrome, small intestinal bacterial overgrowth, Crohn's disease, and/or pancreatic insufficiency. It has been reported that rifaximin is characterized by a negligible systemic absorption, due to its chemical and physical characteristics (Descombe J. J. et al. *Pharmacokinetic study of rifaximin after oral administration in healthy volunteers. Int J Clin Pharmacol Res,* 14 (2), 51-56, (1994)).

Rifaximin is described in Italian Patent IT 1154655 and EP 0161534, both of which are incorporated herein by reference in their entirety for all purposes. EP 0161534 discloses a process for rifaximin production using rifamycin O as the starting material (The Merck Index, XIII Ed., 8301). U.S. Pat. No. 7,045,620 B1 and PCT Publication WO 2006/094662 A1 disclose polymorphic forms of rifaximin.

Rifaximin is approved for the treatment of pathologies caused by non-invasive strains of *Escherichia coli,* a microorganism which is not able to penetrate into GI mucosa and therefore remains in contact with gastrointestinal fluids.

SUMMARY

Described herein are polymorphic forms of rifaximin, including Zeta (ζ), Eta (η), Iota (ι), Form Iota-dry (ι-dry), Form Iota-dry' (ι-dry'), and Form B of rifaximin are described herein.

According to one aspect, polymorphic Form ζ, Form η, Form ι, Form ι-dry, Form ι-dry', or Form B of rifaximin are presented herein.

In one embodiment, polymorph Form ζ exhibits an X-ray powder diffraction pattern having characteristic peaks expressed in degrees 2θ (+/−0.20 degree θ) comprising 4.69, 7.63, 12.52, 13.87.

In one embodiment, polymorph Form ζ of rifaximin comprises an XRPD pattern as substantially depicted in FIG. 4 or FIG. 15 wherein peaks in the XRPD patterns have a variation of +/−0.2 theta.

In one embodiment, polymorph Form η exhibits an X-ray powder diffraction pattern having characteristic peaks expressed in degrees 2θ (+/−0.20 degree θ) comprising 6.1, 7.3, and 7.5 degrees 2-θ; or 6.1, 7.3, and 7.9 degrees 2-θ; 5.3, 6.1, 7.3, 7.5, 8.8, and 12.7 degrees 2-θ; or 5.3, 6.1, 7.3, 7.9, 8.8, and 12.7 degrees 2-θ; or 5.3, 6.1, 7.3, 7.5, 7.9, 8.8, 12.7 degrees 2-θ; or 6.1, 7.3, 7.5, 7.9, 8.8, and 12.7 degrees 2-θ.

In one embodiment, polymorph Form ι exhibits an X-ray powder diffraction pattern having characteristic peaks expressed in degrees 2θ (+/−0.20 degree θ) comprising 5.49, 5.88, 7.86, 9.03, 12.66, and 13.89.

In one embodiment, Form ι exhibits an X-ray powder diffraction pattern having characteristic peaks expressed in degrees 2θ (+/−0.20 degree θ) comprising 5.9; 7.9; 9.0; or 12.7; 13.9; 14.9; or 5.9; 7.9; 12.7; or 5.9; 9.0; 12.7; or 5.9; 13.9; 14.9; or 5.9; 7.9; 14.9; or 9.0; 12.7; 14.9; or 5.9; 7.9; 9.0; 14.9; or 5.9; 7.9; 9.0; 12.7; or 5.9; 7.9; 9.0; 12.7; 13.9; 14.9.

In one embodiment, polymorph Form ι of rifaximin comprises an XRPD pattern as substantially depicted in FIG. 3 or FIG. 9 wherein peaks in the XRPD patterns have a variation of +/−0.2 theta.

In one embodiment, polymorph Form ι of rifaximin compromises thermal data as substantially depicted in FIG. 10 or proton NMR spectrum as substantially depicted in FIG. 12 or vapor data as substantially depicted in FIG. 11 or FT-IR spectrum as substantially depicted in FIG. 13.

In one embodiment, Form ι is formulated into a pharmaceutically acceptable dosage form.

In one embodiment, From ι-dry exhibits an X-ray powder diffraction pattern having characteristic peaks expressed in degrees 2θ (+/−0.10 degree θ) comprising 6.04, 7.90, 8.92, 9.49, 12.76, and 14.14.

In one embodiment, Form ι-dry of rifaximin comprises an XRPD pattern as substantially depicted in FIG. 1 or FIG. 6 or thermal data as substantially depicted in FIG. 7.

In one embodiment, polymorph Form ι-dry is formulated into a pharmaceutically acceptable dosage form.

In one embodiment, polymorph From ι-dry' exhibits an X-ray powder diffraction pattern having characteristic peaks expressed in degrees 2θ (+/−0.15 degree θ) comprising 6.16, 7.92, 8.89, 9.55, 12.80, and 14.25.

In one embodiment, polymorph Form ι-dry' comprises an XRPD pattern as substantially depicted in FIG. 2 or FIG. 8 wherein peaks in the XRPD patterns have a variation of +/−0.15 theta.

In one embodiment, polymorph From ι-dry' is formulated into a pharmaceutically acceptable dosage form.

In one embodiment, polymorph From B exhibits an X-ray powder diffraction pattern having characteristic peaks expressed in degrees 2θ (+/−0.15 degree θ) comprising 5.24, 6.84, 7.74, 8.71, 10.16, and 12.21.

In one embodiment, polymorph Form B comprises an XRPD pattern as substantially depicted in FIG. 6 wherein peaks in the XRPD patterns have a variation of +/−0.15 theta or having DSC or TGA thermograms as substantially depicted in FIG. 17.

In one embodiment, the polymorphs comprise from between about 50 to about 100% pure polymorphous forms before or after formulation.

In one embodiment, the polymorphs comprise from between about 75 to about 100% pure polymorphous forms before or after formulation.

According to one aspect, provided herein are pharmaceutical dosage forms comprising one or more of polymorphic Form ζ, Form η, Form ι, Form ι-dry, Form ι-dry', or Form B of rifaximin or mixtures thereof.

Other embodiment and aspects are disclosed infra.

DETAILED DESCRIPTION

Embodiments of the invention relate to the discovery of new polymorphic forms of rifaximin and the use of those forms as antibiotics. In one embodiment the use of Form ζ, Form η, Form ι, Form Iota-dry, Form Iota-dry' and Form B, of the antibiotic known as Rifaximin (INN), in the manufacture of medicinal preparations for the oral or topical route is contemplated. Embodiments of the invention also relate to administration of such medicinal preparations to a subject in need of treatment with antibiotics.

The different forms of Rifaximin described herein can be made by the methods set forth, for example, in the Examples section. Moreover, polymorphic forms of Rifaximin can be converted to one or more other polymorphic forms of Rifaximin by subjecting them to conditions such as those set forth in the examples.

Rifaximin is a compound of the rifamycin class of antibiotics. Rifaximin is a compound having the structure of Formula I:

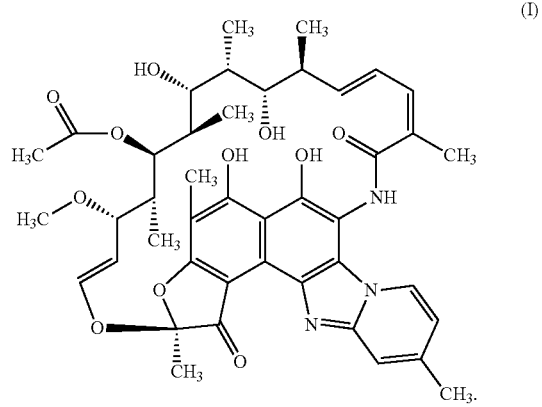 [SMILES: CO[C@H]1/C=C/O[C@@]2(C)Oc3c(C)c(O)c4c(O)c(c5c(nc6cc(C)ccn65)c4c3C2=O)NC(=O)/C(C)=C\C=C\[C@H](C)[C@H](O)[C@@H](C)[C@@H](O)[C@@H](C)[C@H](OC(C)=O)[C@@H]1C]

As used herein, "rifaximin Form ζ," "Form ζ" "Form of rifaximin," "polymorph ζ," and "rifaximin ζ" are used interchangeably to denote the polymorphic form of rifaximin as further described herein by, for example, one or more peaks of an x-ray diffractogram, differential scanning calorimetry data. Form ζ comprises an x-ray powder diffraction pattern peak positions as described herein and in the Figures and Tables. Form ζ may be identified and characterized by one or more of these parameters and/or one or more of the peaks or points in the ranges.

Figure 1:
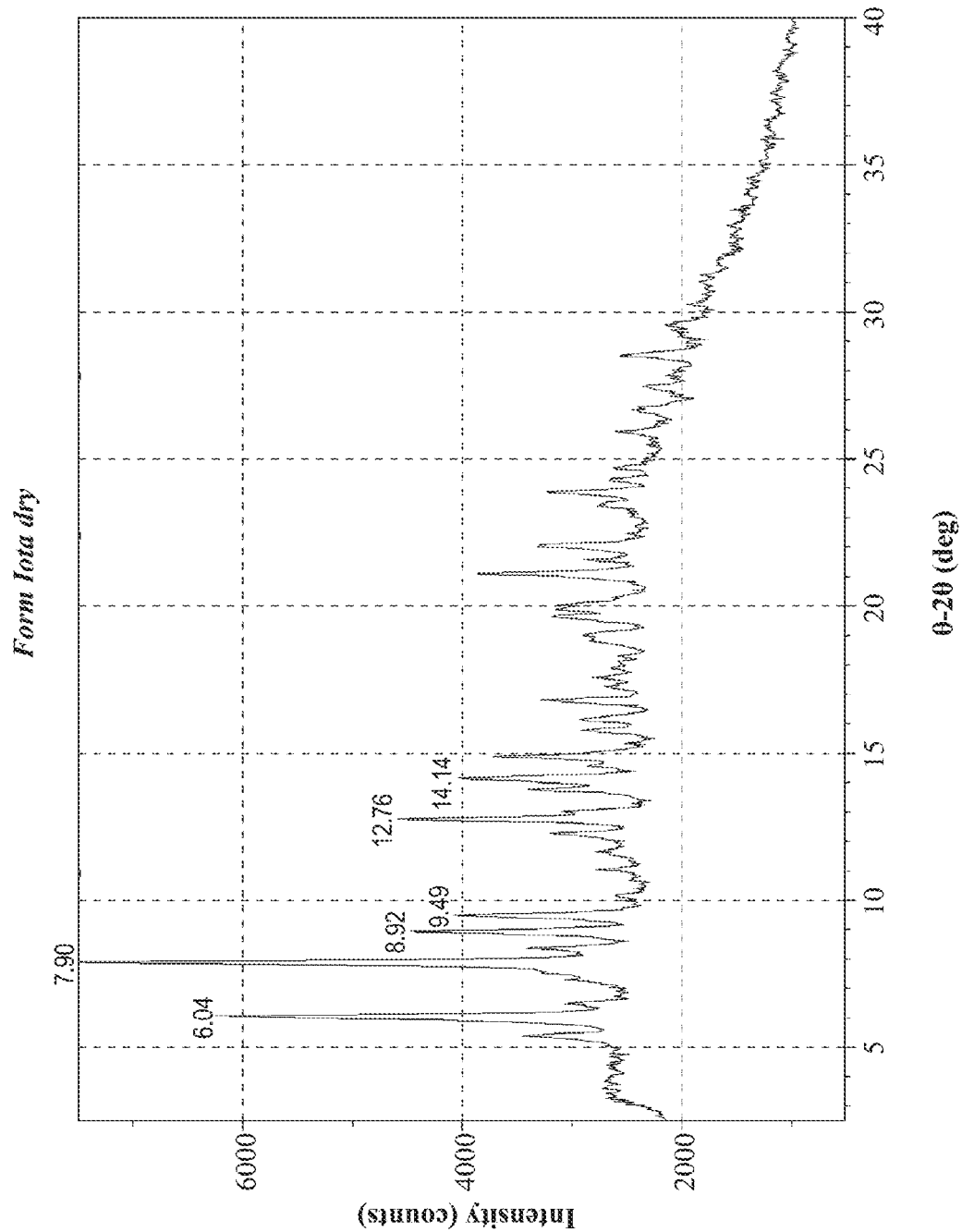
FIG. 1 is an exemplary XRPD pattern of Form Iota dry.
Figure 2:
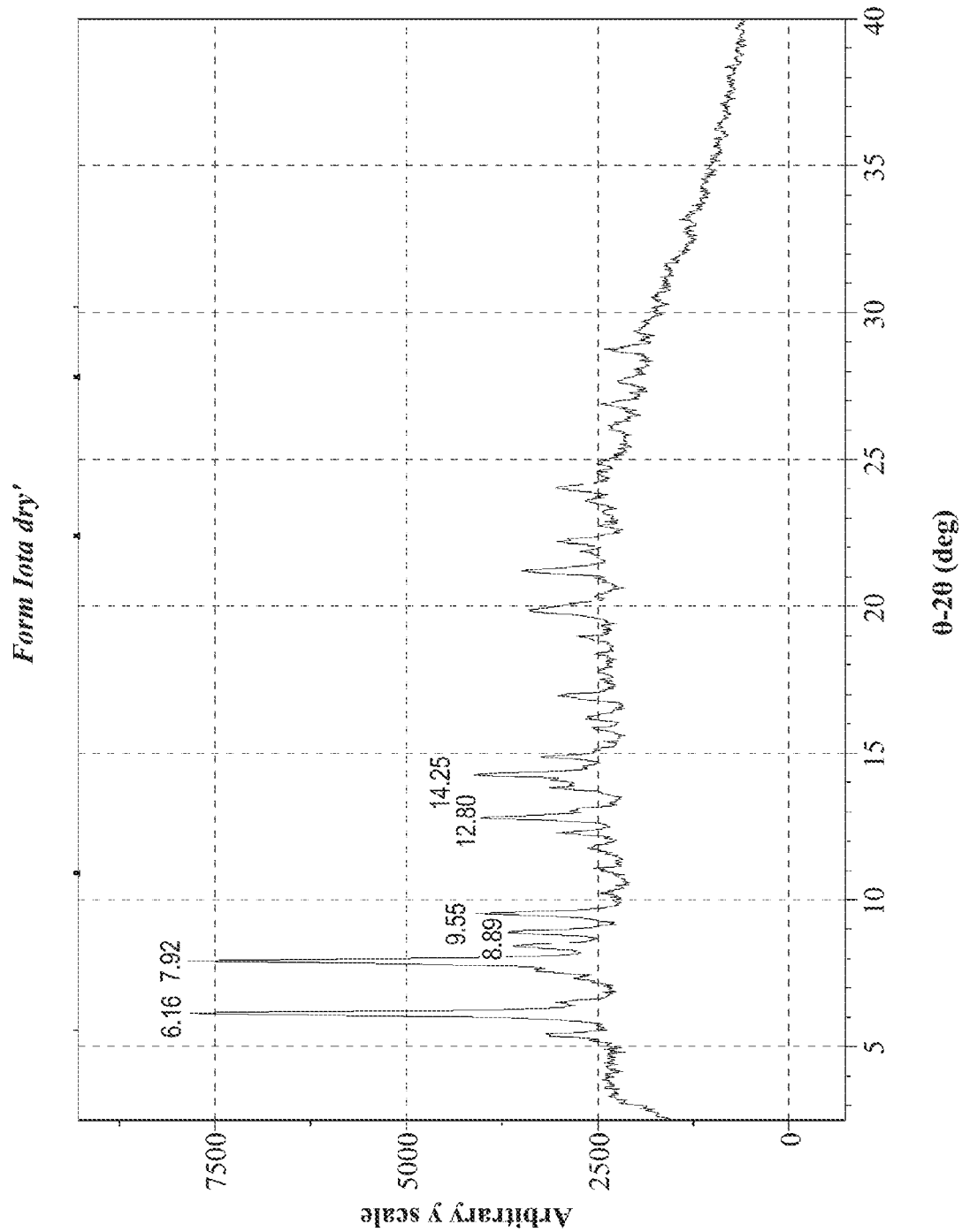
FIG. 2 is an exemplary XRPD pattern of Form Iota dry'.
Figure 3:
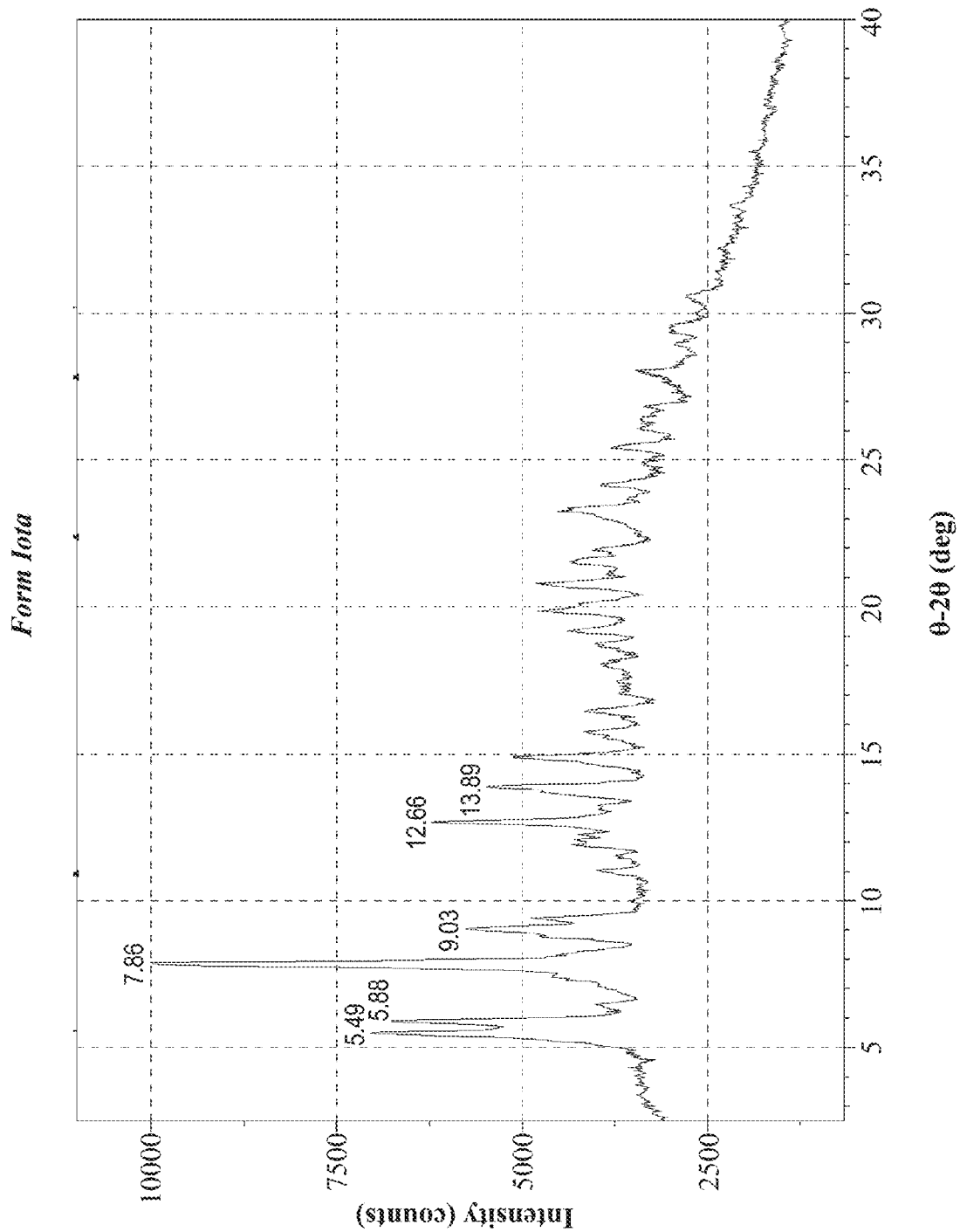
FIG. 3 is an exemplary XRPD pattern of Form Iota.
Figure 4:
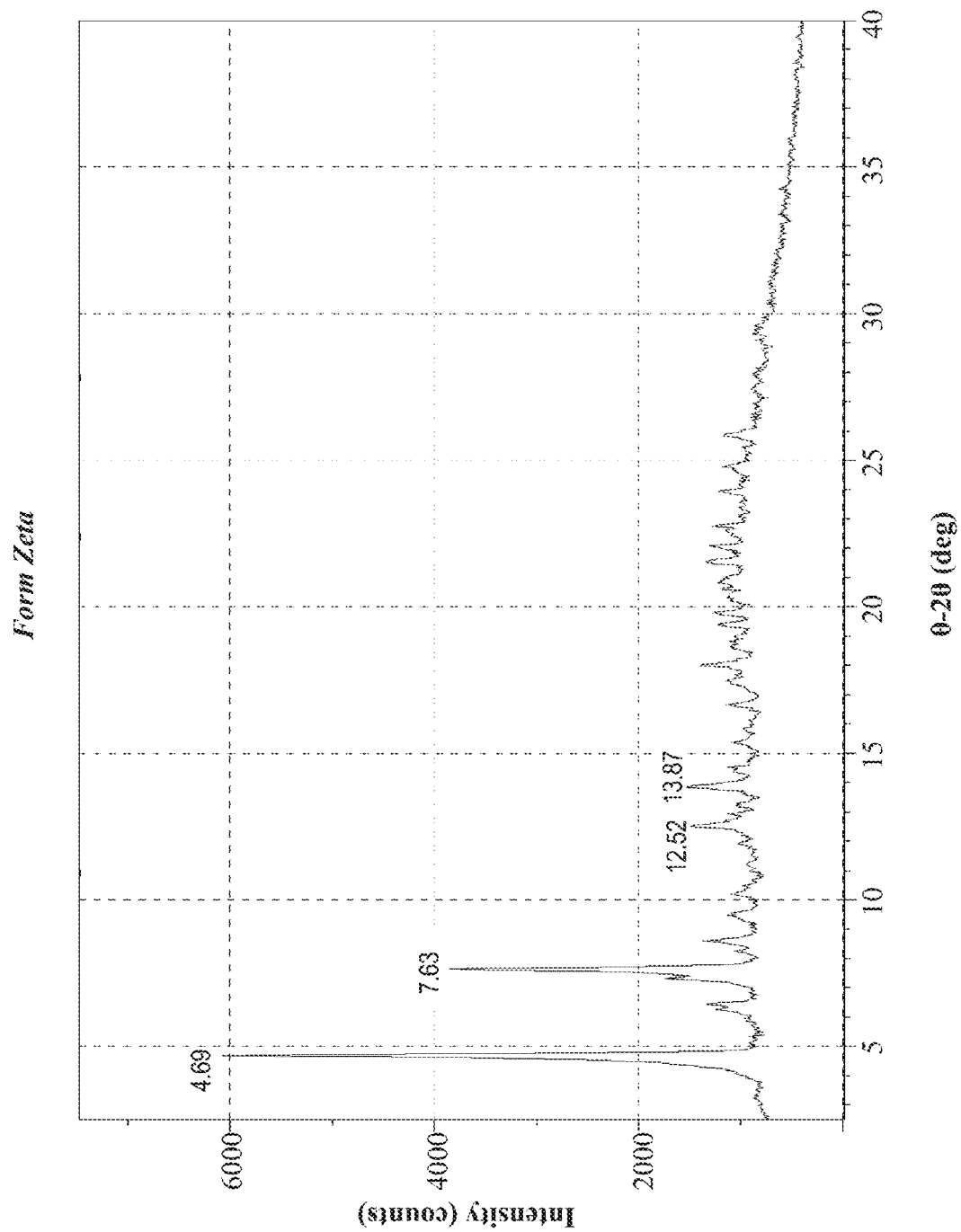
FIG. 4 is an exemplary XRPD pattern of Form Zeta.
Figure 5:
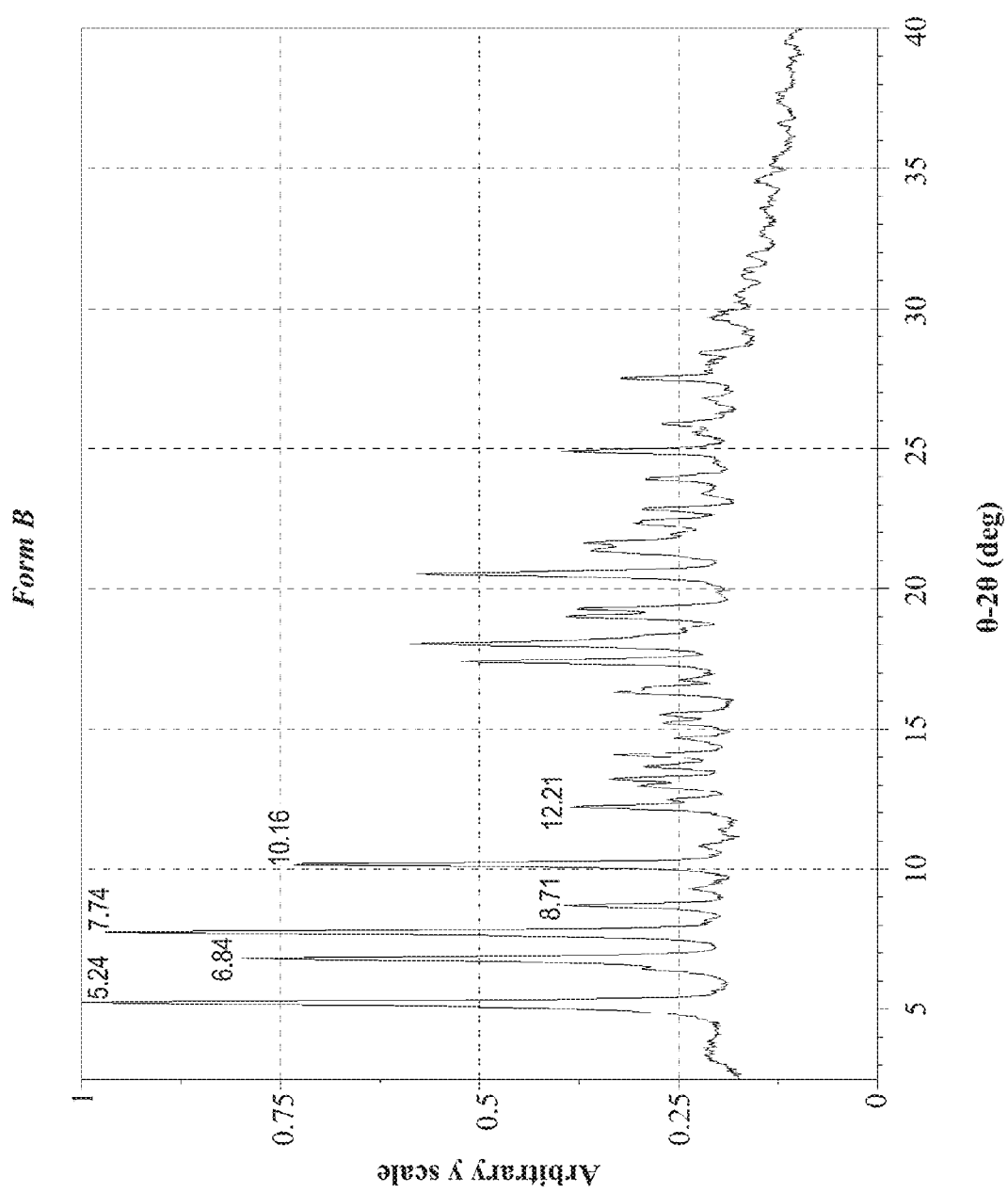
FIG. 5 is an exemplary XRPD pattern of Form B (formerly β-1, β-2).
Figure 6:
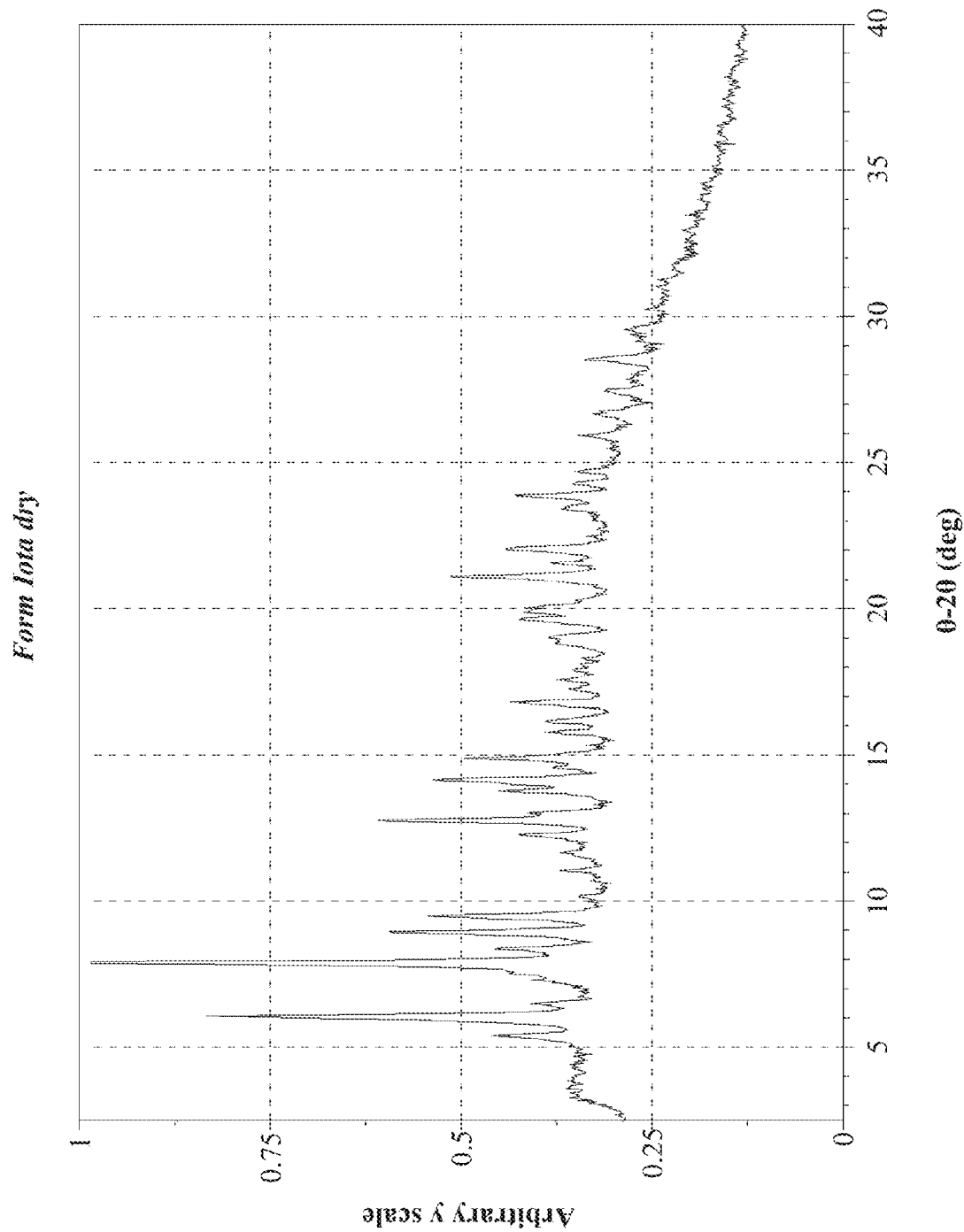
FIG. 6 is an exemplary XRPD pattern of Form Iota dry.
Figure 7:
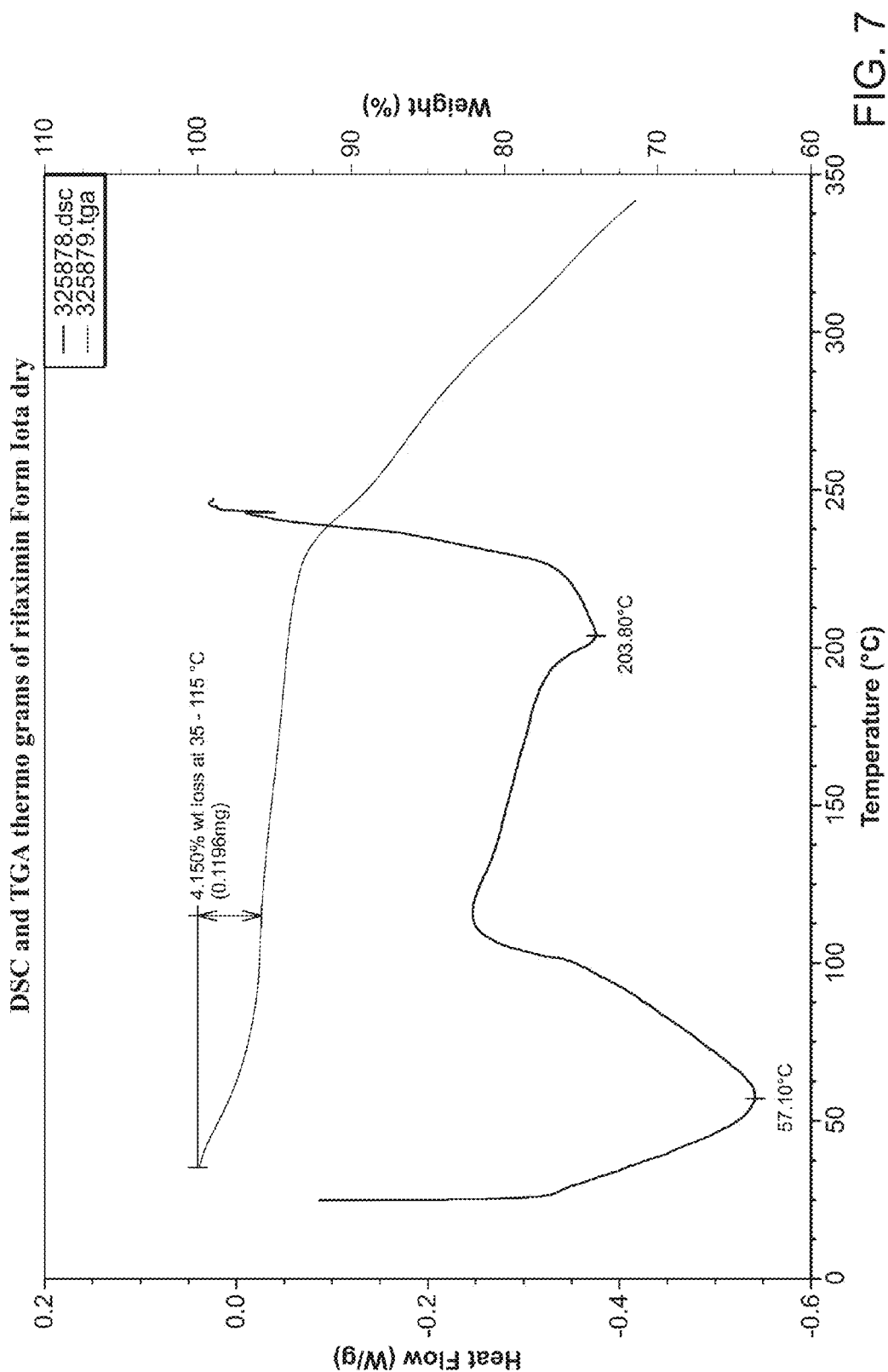
FIG. 7 is an exemplary DSC and TGA thermo grams of rifaximin Form Iota dry.
Figure 8:
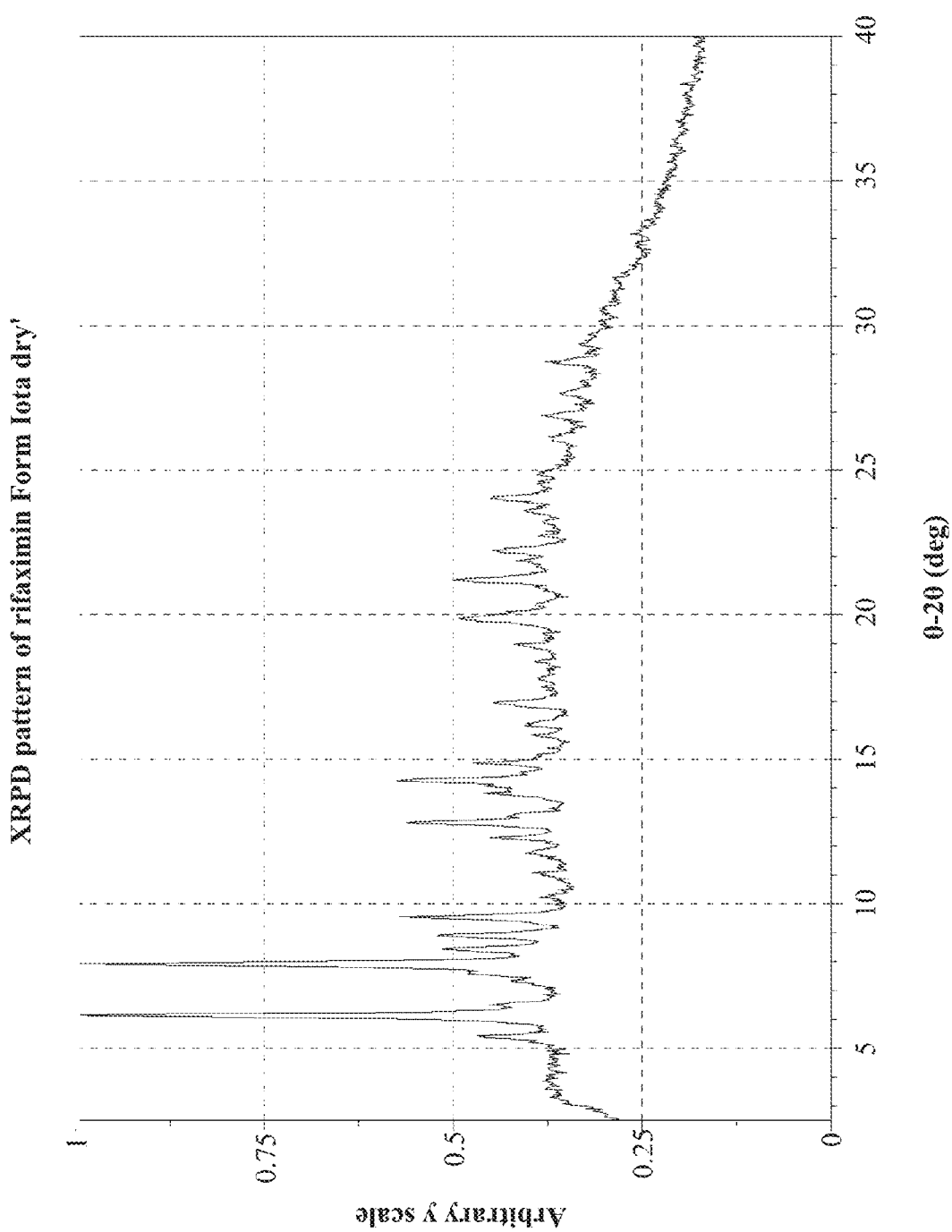
FIG. 8 is an exemplary XRPD pattern of rifaximin Form Iota dry'.
Figure 9:
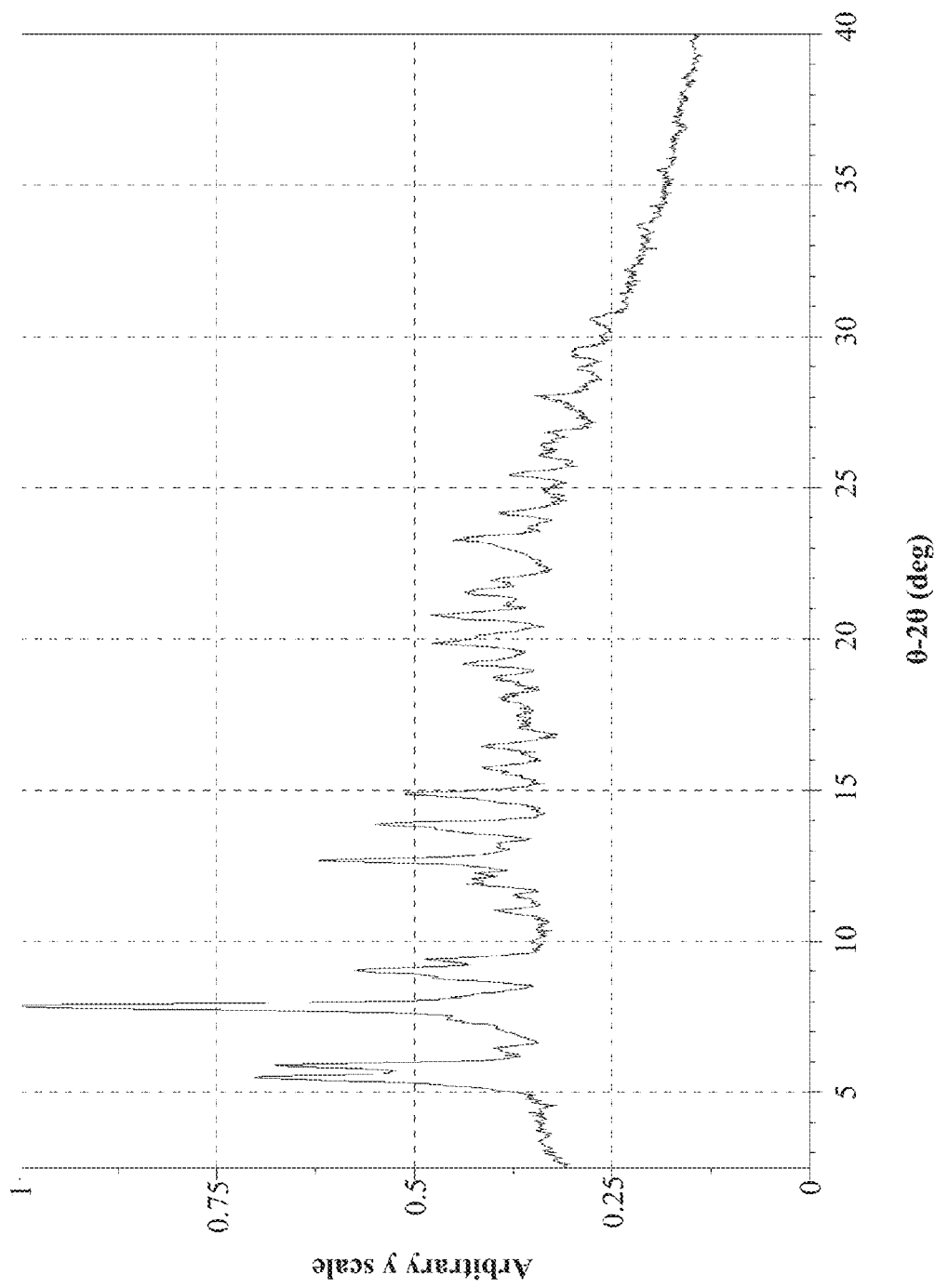
FIG. 9 is an exemplary XRPD pattern of rifaximin Form Iota.
Figure 10:
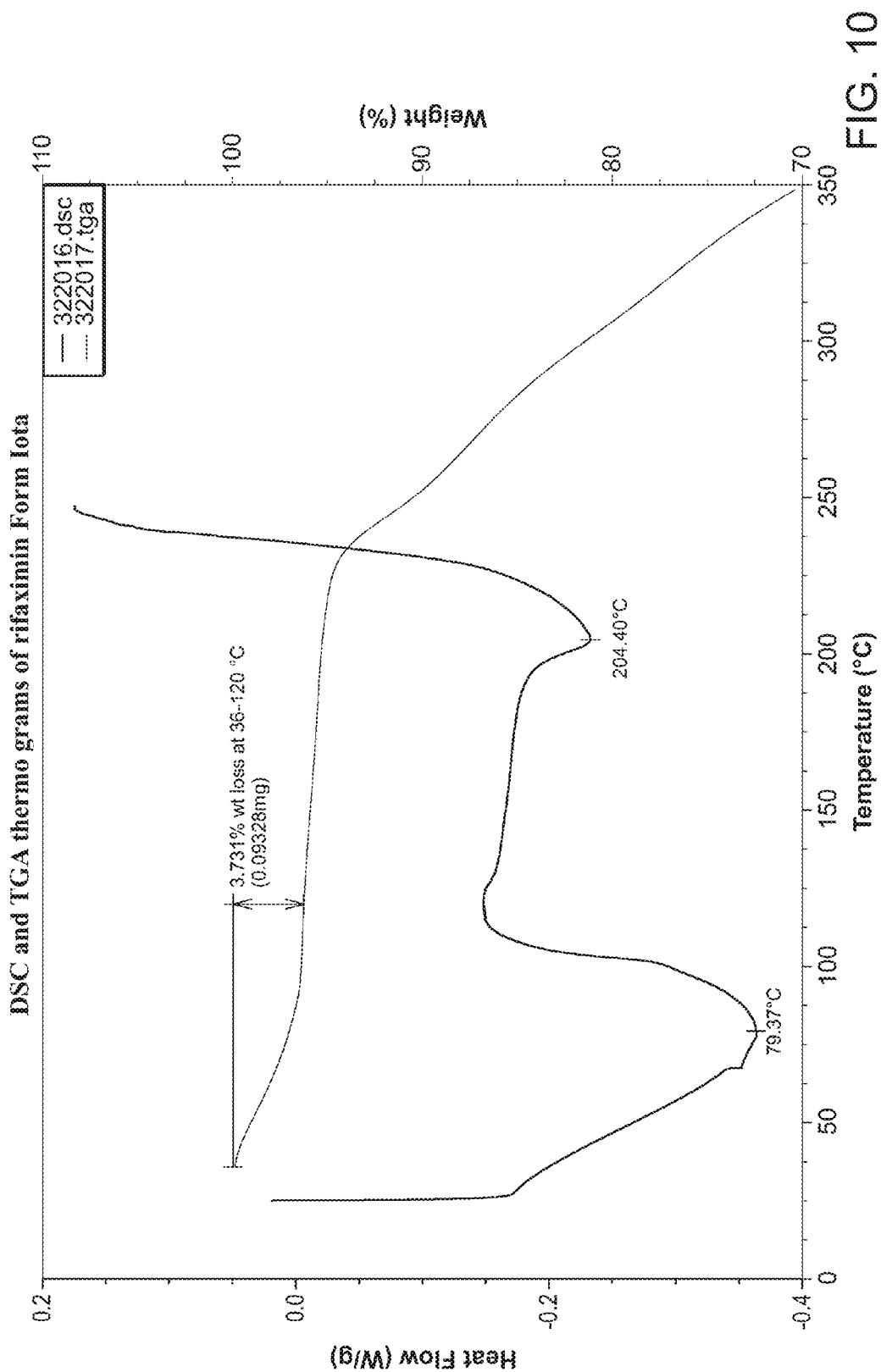
FIG. 10 shows exemplary DSC and TGA thermo grams of rifaximin Form Iota.
Figure 11:
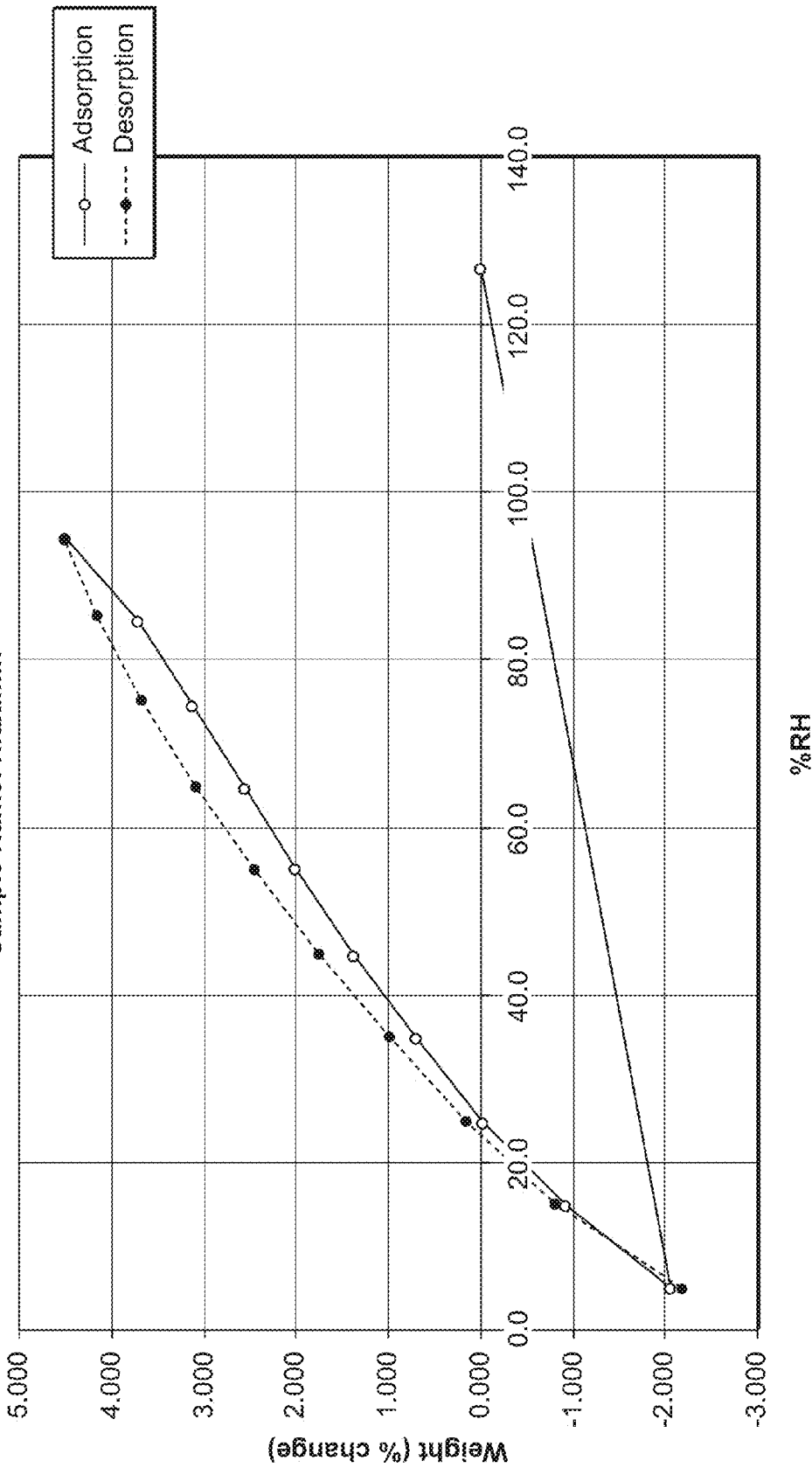
FIG. 11 is an exemplary dynamic vapor sorption/desorption of rifaximin Form Iota.
Figure 12:
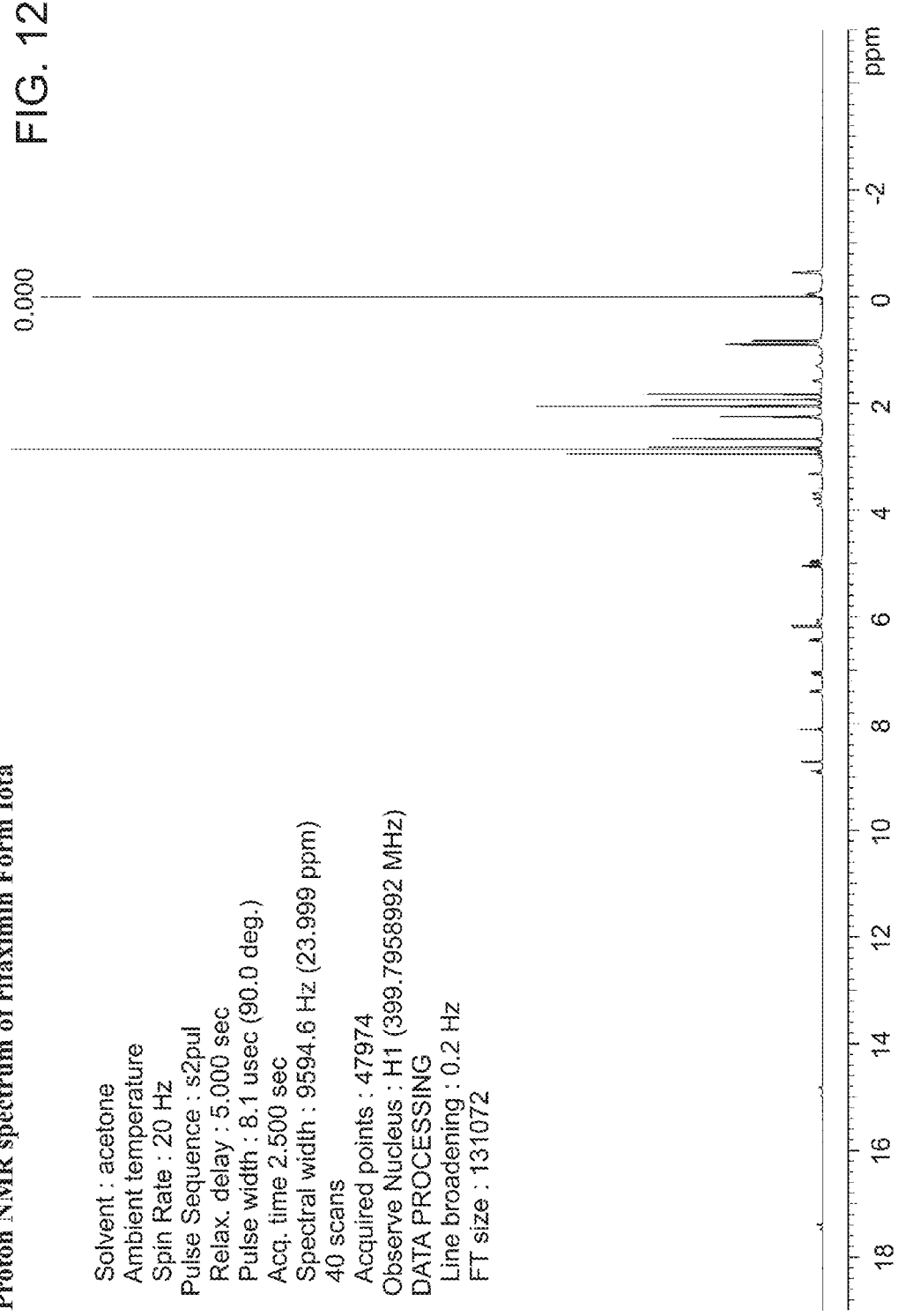
FIG. 12 is an exemplary proton NMR spectrum of rifaximin Form Iota.
Figure 13:
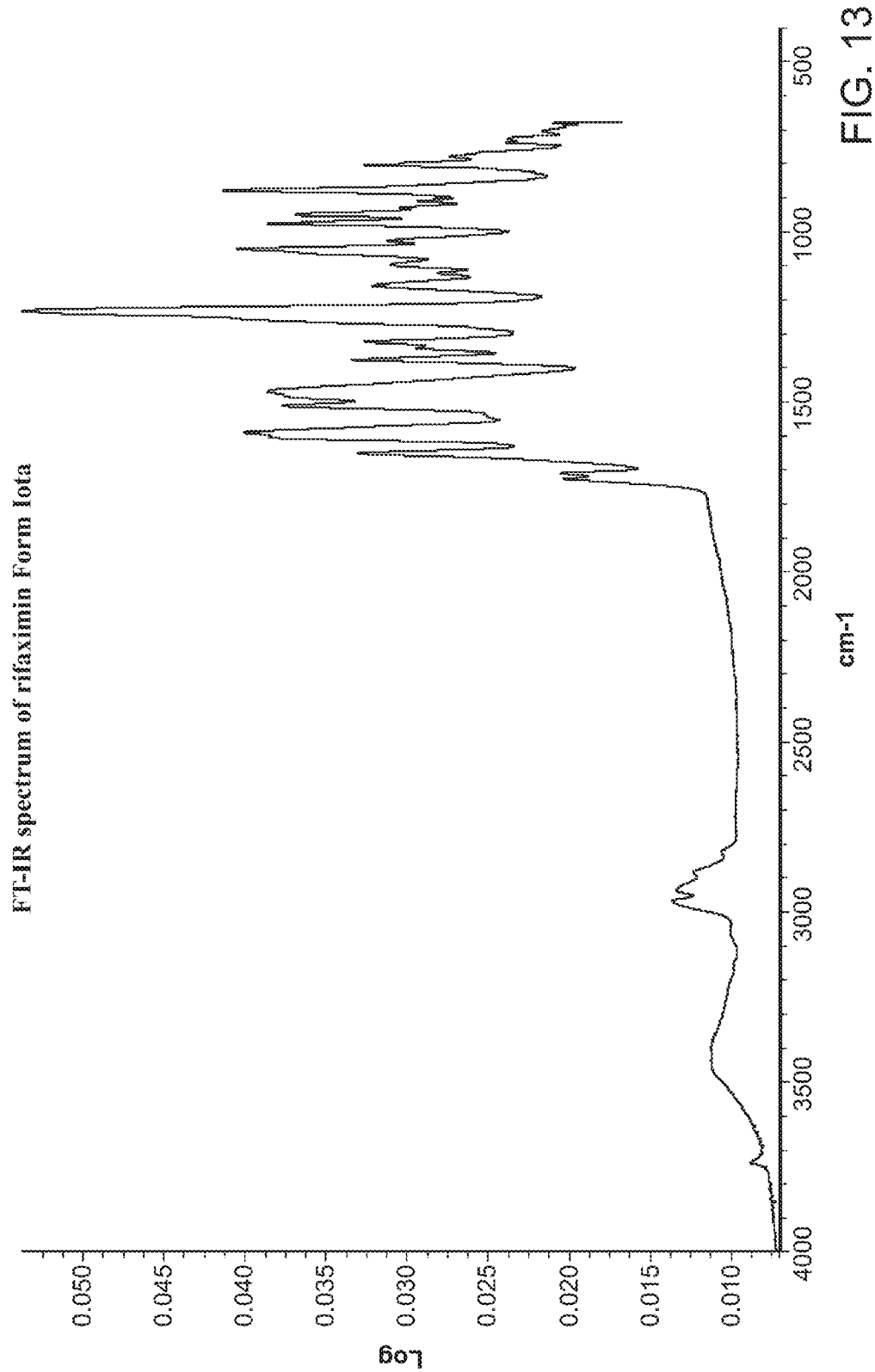
FIG. 13 is an exemplary FT-IR spectrum of rifaximin Form Iota.
Figure 14:
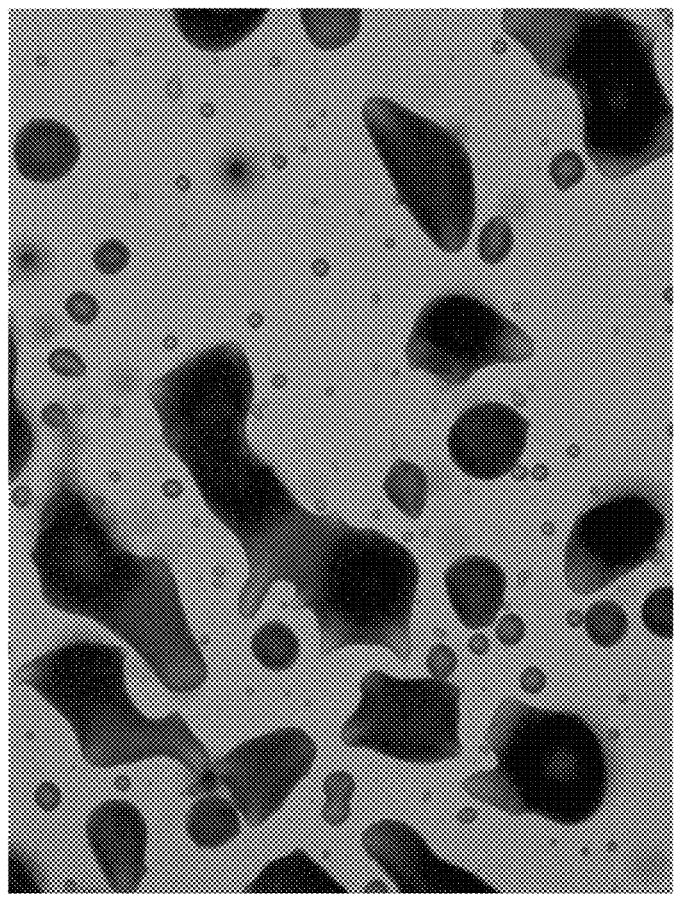
FIG. 14 depicts exemplary hot stage images for rifaximin Form ι.
Figure 15:
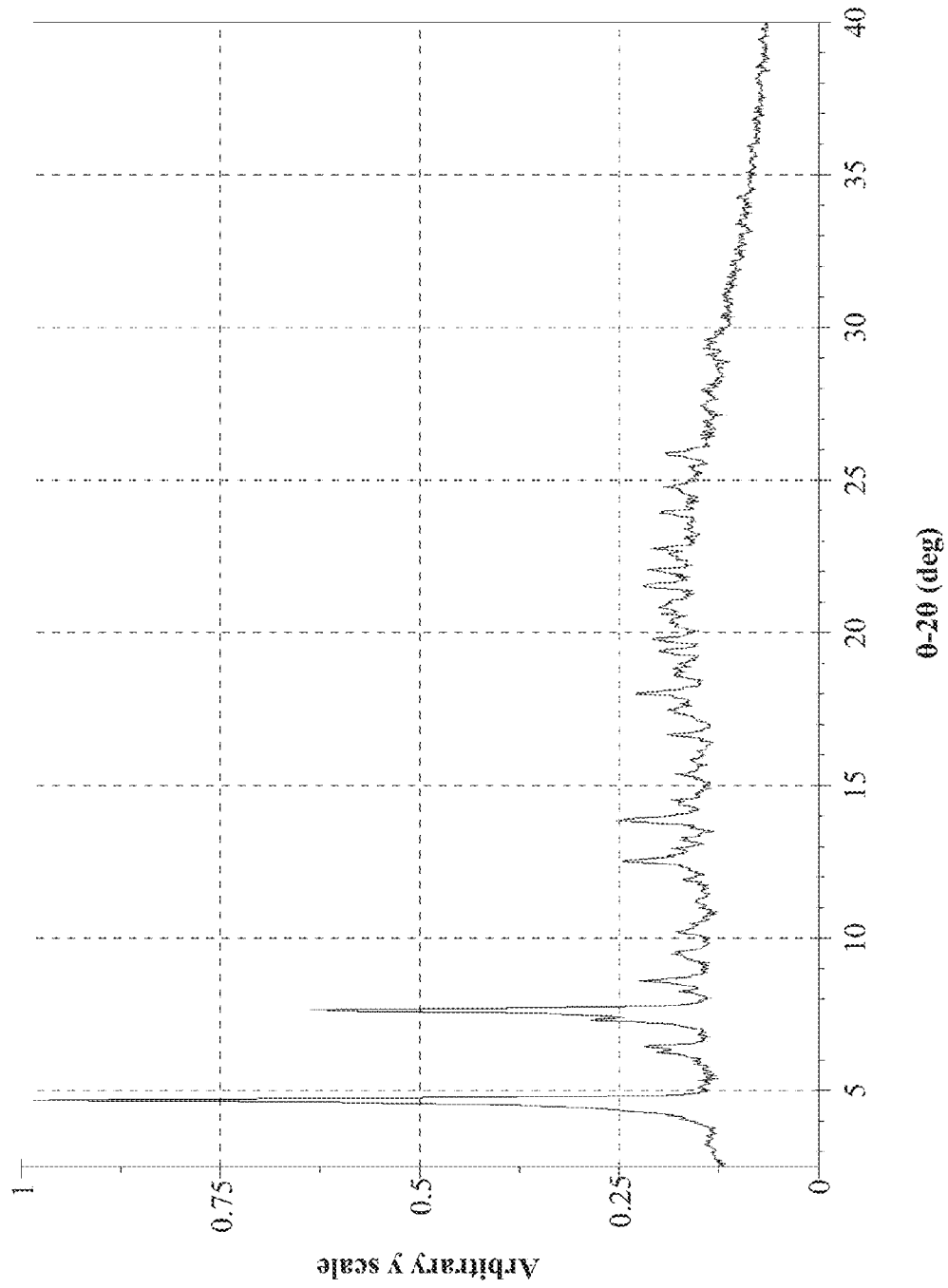
FIG. 15 is an exemplary XRPD pattern of rifaximin Form Zeta.
Figure 16:
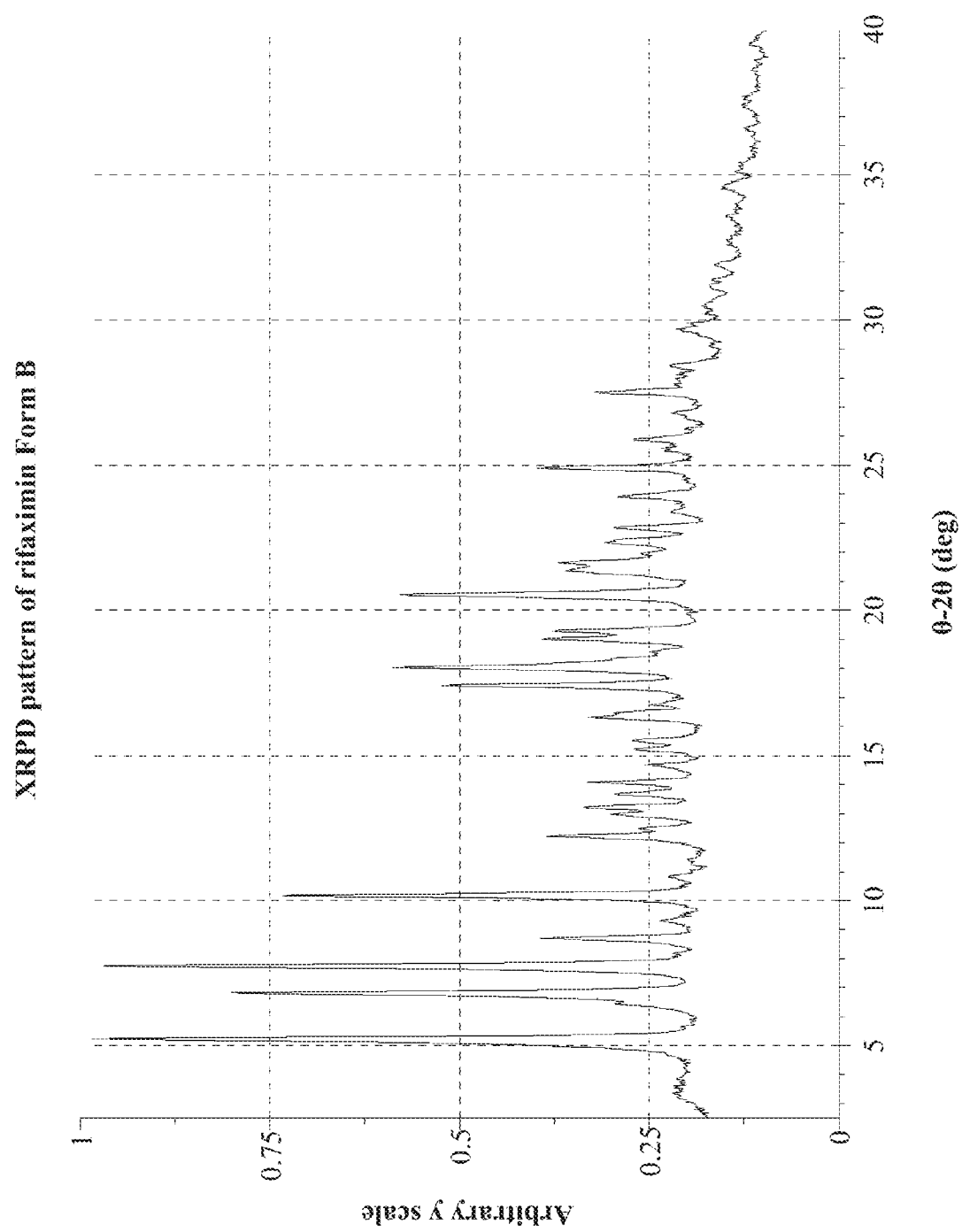
FIG. 16 is an exemplary XRPD pattern of rifaximin Form B.
Figure 17:
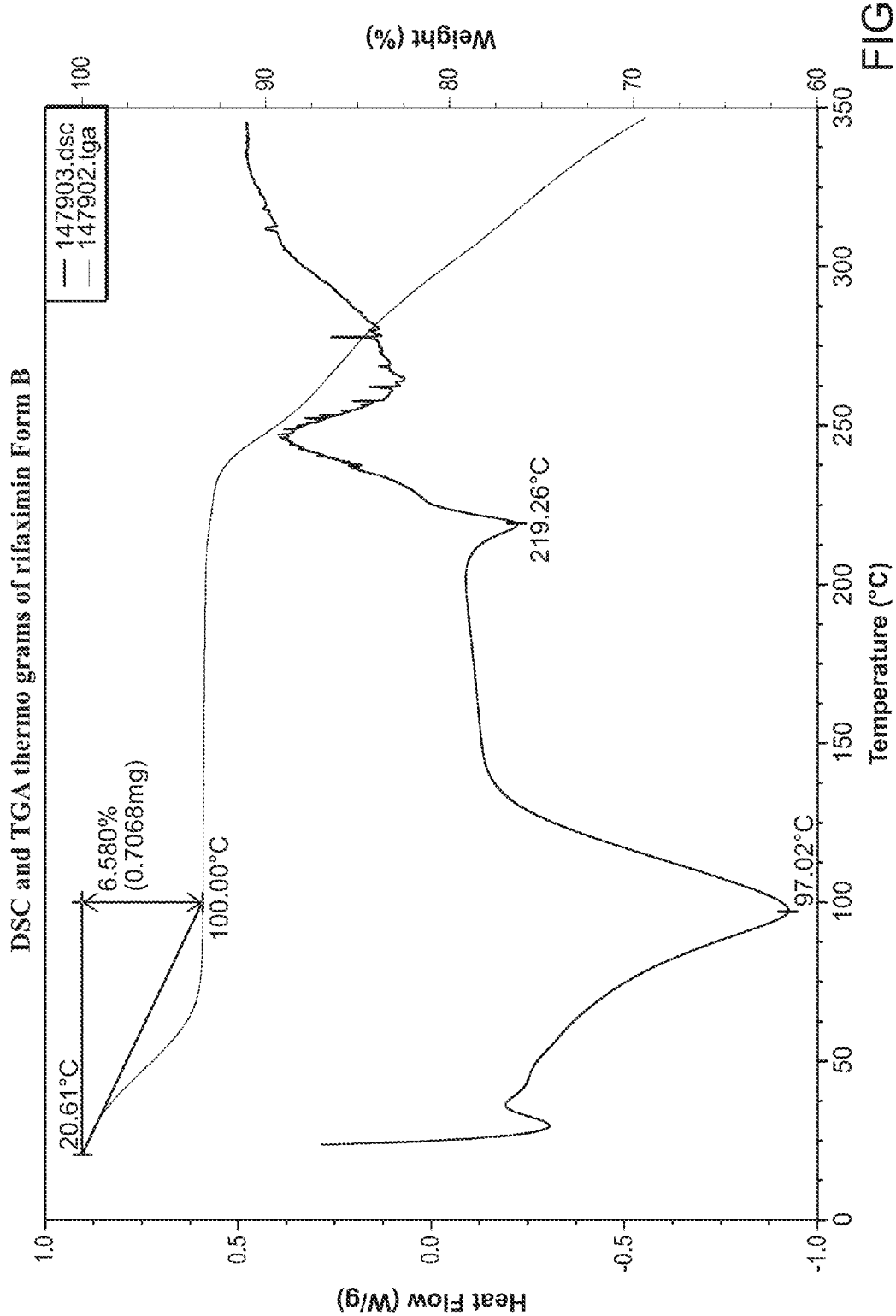
FIG. 17 shows exemplary DSC and TGA thermograms of rifaximin Form B.
Figure 18:
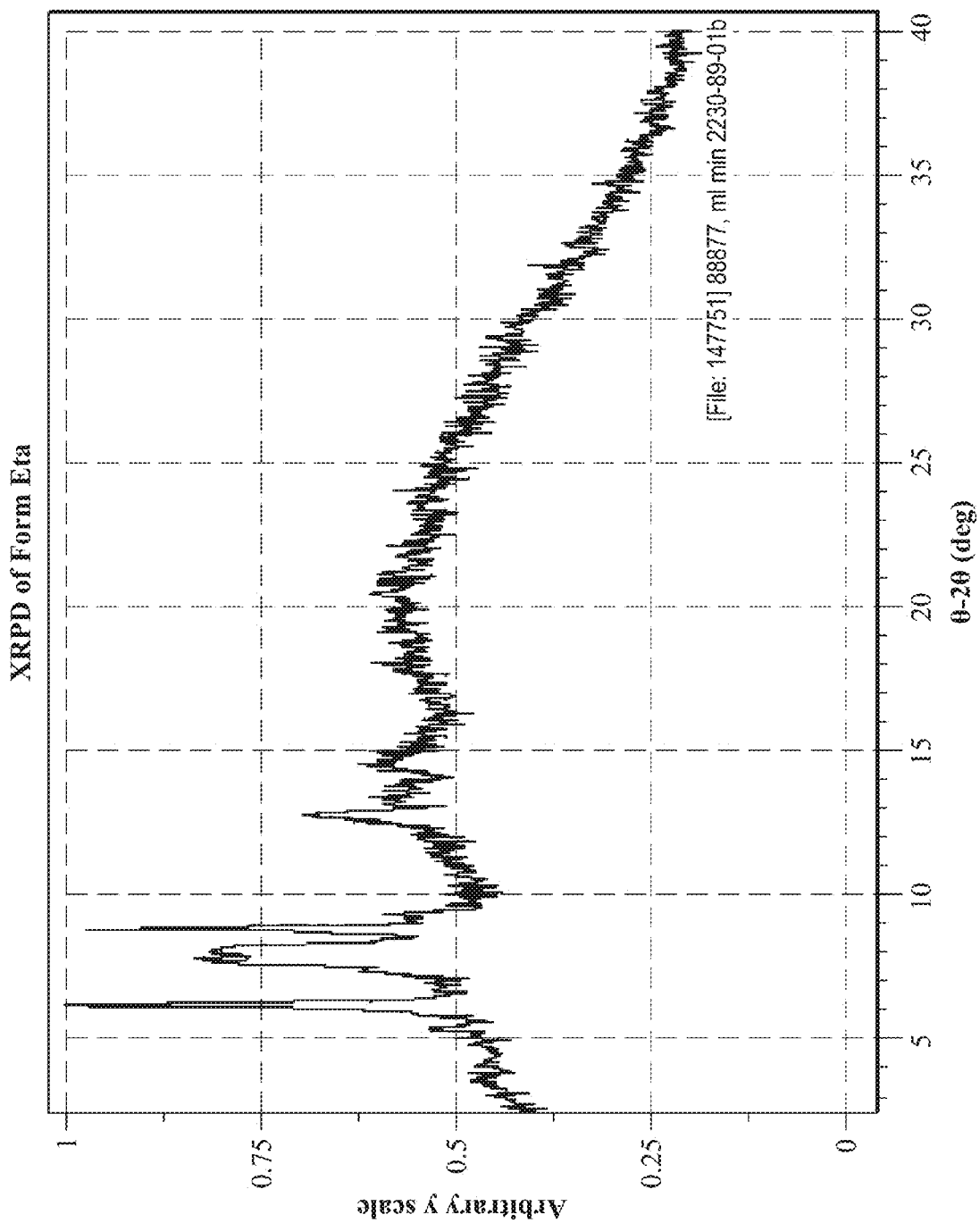
FIG. 18 is an exemplary XRPD pattern of rifaximin Form Eta.

As used herein, "rifaximin Form η," "Form η," "polymorph η," "Form η of rifaximin" and "rifaximin η" if are used interchangeably to denote the polymorphic form of rifaximin as further described herein by, for example, one or more peaks of an x-ray diffractogram (FIG. 18) and methods of making such form. Form η comprises an x-ray powder diffraction pattern peak positions as described herein and in the Figures and Tables. Form η may be identified and characterized by one or more of these parameters and/or one or more of the peaks or points in the ranges.

As used herein, "rifaximin Form ι," "Form ι," "polymorph ι," "Form ι of rifaximin" and "rifaximin ι" are used interchangeably to denote the polymorphic form of rifaximin as further described herein by, for example, one or more peaks of an x-ray diffractogram, NMR, thermal data, or hot stage microscopy and methods of making such form. Form ι comprises x-ray powder diffraction pattern peak positions described herein and in the Figures and Tables. Form ι may be identified and characterized by one or more of these parameters and/or one or more of the peaks or points in the ranges.

As used herein, "rifaximin Form ι-dry," "Form ι-dry," "polymorph ι-dry," "Form ι-dry of rifaximin" and "rifaximin ι-dry" are used interchangeably to denote the polymorphic form of rifaximin as further described herein by, for example, one or more peaks of an x-ray diffractogram, NMR, thermal data, or hot stage microscopy and methods of making such form. Form ι-dry comprises x-ray powder diffraction pattern peak positions described herein and in the Figures and Tables. Form ι-dry may be identified and characterized by one or more of these parameters and/or one or more of the peaks or points in the ranges.

As used herein, "rifaximin Form ι-dry'," "Form ι-dry'," "polymorph ι-dry'," "Form ι-dry' of rifaximin" and "rifaximin ι-dry'" are used interchangeably to denote the polymorphic form of rifaximin as further described herein by, for example, one or more peaks of an x-ray diffractogram, NMR, thermal data, or hot stage microscopy and methods of making such form. Form ι-dry' comprises x-ray powder diffraction pattern peak positions described herein and in the Figures. Form ι-dry' may be identified and characterized by one or more of these parameters and/or one or more of the peaks or points in the ranges.

As used herein, "rifaximin Form B," "Form B," "polymorph B," "Form B of rifaximin" and "rifaximin B" are used interchangeably to denote the polymorphic form of rifaximin as further described herein by, for example, one or more peaks of an x-ray diffractogram, NMR, thermal data, or hot stage microscopy and methods of making such form. Form B comprises x-ray powder diffraction pattern peak positions described herein and in the Figures. Form B may be identified and characterized by one or more of these parameters and/or one or more of the peaks or points in the ranges.

As used herein, the term polymorph is occasionally used as a general term in reference to the forms of rifaximin and includes within the context, salt, hydrate, polymorph forms of rifaximin disclosed herein. This use depends on context and will be clear to one of skill in the art.

As used herein, the term "about" when used in reference to x-ray powder diffraction pattern peak positions refers to the inherent variability of the peaks depending on, for example, the calibration of the equipment used, the process used to produce the polymorph, the age of the crystallized material and the like, depending on the instrumentation used. In this case the measure variability of the instrument was about ±0.2 degrees 2-θ. A person skilled in the art, having the benefit of this disclosure, would understand the use of "about" in this context. The term "about" in reference to other defined parameters, e.g., water content, $C_{max}$, $t_{max}$, AUC, intrinsic dissolution rates, temperature, and time, indicates the inherent variability in, for example, measuring the parameter or achieving the parameter. A person skilled in the art, having the benefit of this disclosure, would understand the variability of a parameter as connoted by the use of the word about.

Polymorphism, as used herein, refers to the occurrence of different crystalline forms of a single compound in distinct hydrate status, e.g., a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as solubility profiles, melting point temperatures, hygroscopicity, particle shape, density, flowability, compactibility and/or x-ray diffraction peaks. The solubility of each polymorph may vary, thus, identifying the existence of pharmaceutical polymorphs is essential for providing pharmaceuticals with predictable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction spectroscopy and by other methods such as, infrared spectrometry. For a general review of polymorphs and the pharmaceutical applications of polymorphs see G. M. Wall, Pharm Manuf. 3, 33 (1986); J. K. Haleblian and W. McCrone, J Pharm. Sci., 58, 911 (1969); and J. K. Haleblian, J. Pharm. Sci., 64, 1269 (1975), all of which are incorporated herein by reference.

As used herein, "subject" includes organisms which are capable of suffering from a bowel disorder or other disorder treatable by rifaximin or who could otherwise benefit from the administration of a rifaximin as described herein, such as human and non-human animals. Preferred human animals include human subjects. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc. Susceptible to a bowel disorder is meant to include subjects at risk of developing a bowel disorder infection, i.e., subjects suffering from immune suppression, subjects that have been exposed to other subjects with a bacterial infection, physicians, nurses, subjects traveling to remote areas known to harbor bacteria that causes travelers' diarrhea, etc.

The language "a prophylactically effective amount" of a compound refers to an amount of a compound of the invention of formula (I) or otherwise described herein which is effective, upon single or multiple dose administration to the subject, in preventing or treating a bacterial infection.

The language "therapeutically effective amount" of a compound of the invention refers to an amount of an agent which is effective, upon single or multiple dose administration to the subject to provide a therapeutic benefit to the subject. In one embodiment, the therapeutic benefit is inhibiting a virus, or in prolonging the survivability of a subject with such a viral infection. In another embodiment, the therapeutic benefit is inhibiting a bacterial infection or prolonging the survival of a subject with such a bacterial infection beyond that expected in the absence of such treatment.

Rifaximin exerts a broad antibacterial activity in the gastrointestinal tract against localized gastrointestinal bacteria that cause infectious diarrhea, including anaerobic strains. It has been reported that rifaximin is characterized by a negligible systemic absorption, due to its chemical and physical characteristics (Descombe J. J. et al. *Pharmacokinetic study of rifaximin after oral administration in healthy volunteers. Int J Clin Pharmacol Res,* 14 (2), 51-56, (1994)).

In respect to possible adverse events coupled to the therapeutic use of rifaximin, the induction of bacterial resistance to the antibiotics is of particular relevance.

From this point of view, any differences found in the systemic absorption of forms of rifaximin may be significant because at sub-inhibitory concentration of rifaximin, such as in the range from 0.1 to 1 μg/ml, selection of resistant mutants has been demonstrated to be possible (Marchese A. et al. *In vitro activity of rifaximin, metronidazole and vancomycin against clostridium difficile and the rate of selection of spontaneously resistant mutants against representative anaerobic and aerobic bacteria, including ammonia producing species. Chemotherapy,* 46(4), 253-266, (2000)).

Polymorphs of rifaximin have been found to have differing in vivo bioavailability properties. Thus, the polymorphs disclosed herein would be useful in the preparation of pharmaceuticals with different characteristics for the treatment of infections. This would allow generation of rifaximin preparations that have significantly different levels of adsorption with $C_{max}$ values from about 0.0 ng/ml to 5.0 μg/ml. This leads to preparation of rifaximin compositions that are from negligibly to significantly adsorbed by subjects undergoing treatment. One embodiment of the invention is modulating the therapeutic action of rifaximin by selecting the proper polymorphic form, or mixture of forms, for treatment of a patient. For example, in the case of invasive bacteria, the most bioavailable polymorphic form can be selected from those disclosed herein, whereas in case of non-invasive pathogens less adsorbed forms of rifaximin can be selected, since they may be safer for the subject undergoing treatment.

The above-mentioned novel forms of rifaximin can be advantageously used as pure and homogeneous products in the manufacture of medicinal preparations containing rifaximin.

Some features of polymorph Form include, for example:

Form ζ, comprises X-ray powder diffraction pattern having characteristic peaks expressed degrees 2θ (+/−0.20 degree θ) at 4.69, 7.63, 12.52, and 13.87.

Form ζ comprises X-ray powder diffraction pattern having characteristic peaks expressed degrees 2θ (+/−0.20 degree θ) at 4.69, 7.63, and 12.52.

Form ζ, comprises X-ray powder diffraction pattern having characteristic peaks expressed degrees 2θ (+/−0.20 degree θ) at 7.63, 12.52, and 13.87.

Form ζ, comprises X-ray powder diffraction pattern having characteristic peaks expressed degrees 2θ (+/−0.20 degree θ) at 4.69, 12.52, and 13.87.

Form ζ, comprises X-ray powder diffraction pattern having characteristic peaks expressed degrees 2θ (+/−0.20 degree θ) at 4.69, 7.63, and 13.87.

the polymorph Form ζ exhibits an X-ray powder diffraction pattern having characteristic peaks expressed in degrees 2θ (+/−0.20 degree θ) at 4.7 (doublet), 7.6 (doublet), and 9.5 degrees 2-θ; or 4.7 (doublet), 7.3, and 8.2 degrees 2-θ; or 7.6 (doublet), 8.6, and 10.5 degrees 2-θ; or 8.2, 8.6, and 9.5 degrees 2-θ; or 10.2 (triplet), 12.6 (quintet), and 13.2 (doublet) degrees 2-θ; or 7.3, 10.5, and 12.9 (doublet) degrees 2-θ; or 7.3, 7.6 (doublet), 8.2, 8.6 degrees 2-θ; or 4.7 (doublet), 7.3, 7.6 (doublet), 9.5, and 10.5 degrees 2-θ; or 8.2, 8.6, 9.5, 10.2 (triplet), and 10.5 degrees 2-θ; or 8.6, 9.5, 10.2 (triplet), 10.5, and 11.2 (doublet) degrees 2-θ; or 4.7 (doublet), 6.3, 6.4, 7.3, 7.6 (doublet), 8.2, 8.6, 9.5, 10.2 (triplet), 10.5, 11.2 (doublet), 11.9 (doublet), 12.2 (weak), 12.6 (quintet), 12.9 (doublet), 13.2 (doublet) degrees 2-θ.

The polymorph Form ζ exhibits an X-ray powder diffraction pattern having characteristic peaks expressed in degrees 2θ (+/−0.20 degree θ) at 4.7 (doublet), 7.6 (doublet), and 9.5 degrees 2-θ; or 4.7 (doublet), 7.3, and 8.2 degrees 2-θ.

The polymorph Form ζ exhibits an X-ray powder diffraction pattern having characteristic peaks expressed in degrees 2θ (+/−0.20 degree θ) at 7.6 (doublet), 8.6, and 10.5 degrees 2-θ.

The polymorph Form ζ exhibits an X-ray powder diffraction pattern having characteristic peaks expressed in degrees 2θ (+/−0.20 degree θ) at 8.2, 8.6, and 9.5 degrees 2-θ.

The polymorph Form ζ exhibits an X-ray powder diffraction pattern having characteristic peaks expressed in degrees 2θ (+/−0.20 degree θ) at 10.2 (triplet), 12.6 (quintet), and 13.2 (doublet) degrees 2-θ.

The polymorph Form ζ exhibits an X-ray powder diffraction pattern having characteristic peaks expressed in degrees 2θ (+/−0.20 degree θ) at 7.3, 10.5, and 12.9 (doublet) degrees 2-θ.

The polymorph Form ζ exhibits an X-ray powder diffraction pattern having characteristic peaks expressed in degrees 2θ (+/−0.20 degree θ) at 7.3, 7.6 (doublet), 8.2, 8.6 degrees 2-θ.

The polymorph Form ζ exhibits an X-ray powder diffraction pattern having characteristic peaks expressed in degrees 2θ (+/−0.20 degree θ) at 4.7 (doublet), 7.3, 7.6 (doublet), 9.5, and 10.5 degrees 2-θ.

The polymorph Form ζ exhibits an X-ray powder diffraction pattern having characteristic peaks expressed in degrees 2θ (+/−0.20 degree θ) at 8.2, 8.6, 9.5, 10.2 (triplet), and 10.5 degrees 2-θ.

The polymorph Form ζ exhibits an X-ray powder diffraction pattern having characteristic peaks expressed in degrees 2θ (+/−0.20 degree θ) at 8.6, 9.5, 10.2 (triplet), 10.5, and 11.2 (doublet) degrees 2-θ.

The polymorph Form ζ exhibits an X-ray powder diffraction pattern having characteristic peaks expressed in degrees 2θ (+/−0.20 degree θ) at 4.7 (doublet), 6.3, 6.4, 7.3, 7.6 (doublet), 8.2, 8.6, 9.5, 10.2 (triplet), 10.5, 11.2 (doublet), 11.9 (doublet), 12.2 (weak), 12.6 (quintet), 12.9 (doublet), 13.2 (doublet) degrees 2-θ.

Some features of polymorph Form η include, for example:

Form η exhibits an X-ray powder diffraction pattern having characteristic peaks expressed in degrees 2θ (+/−0.20 degree θ) at 6.1, 7.3, and 7.5 degrees 2-θ; or 6.1, 7.3, and 7.9 degrees 2-θ; or 6.1, 7.3, and 8.8 degrees 2-θ; or 6.1, 7.3, and 12.7 degrees 2-θ; or 6.1, 7.5, and 8.8 degrees 2-θ; or 6.1, 7.5, and 7.9 degrees 2-θ; or 5.3, 6.1, and 7.3 degrees 2-θ; or 5.3, 6.1, and 7.9 degrees 2-θ; or 5.3, 6.1, and 12.7 degrees 2-θ; or 5.3, 6.1, and 7.5 degrees 2-θ; or 5.3, 6.1, and 8.8 degrees 2-θ; or 6.1, 7.3, 7.5, 7.9, 8.8, and 12.7 degrees 2-θ; or 5.3, 6.1, 7.3, 7.5, 7.9, 8.8, and 12.7 degrees 2-θ; or 5.3, 6.1, 7.3, 7.5, 8.8, and 12.7 degrees 2-θ; or 5.3, 6.1, 7.3, 7.5, 7.9, 8.8, and 12.7 degrees 2-θ.

Form η exhibits an X-ray powder diffraction pattern having characteristic peaks expressed in degrees 2θ (+/−0.20 degree θ) at 6.1, 7.3, and 7.5 degrees 2-θ; or 6.1, 7.3, and 7.9 degrees 2-θ.

Form η exhibits an X-ray powder diffraction pattern having characteristic peaks expressed in degrees 2θ (+/−0.20 degree θ) at 6.1, 7.3, and 8.8 degrees 2-θ.

Form η exhibits an X-ray powder diffraction pattern having characteristic peaks expressed in degrees 2θ (+/−0.20 degree θ) at 6.1, 7.3, and 12.7 degrees 2-θ.

Form η exhibits an X-ray powder diffraction pattern having characteristic peaks expressed in degrees 2θ (+/−0.20 degree θ) at 6.1, 7.5, and 8.8 degrees 2-θ.

Form η exhibits an X-ray powder diffraction pattern having characteristic peaks expressed in degrees 2θ (+/−0.20 degree θ) at 6.1, 7.5, and 7.9 degrees 2-θ.

Form η exhibits an X-ray powder diffraction pattern having characteristic peaks expressed in degrees 2θ (+/−0.20 degree θ) at 5.3, 6.1, and 7.3 degrees 2-θ.

Form η exhibits an X-ray powder diffraction pattern having characteristic peaks expressed in degrees 2θ (+/−0.20 degree θ) at 5.3, 6.1, and 7.9 degrees 2-θ.

Form η exhibits an X-ray powder diffraction pattern having characteristic peaks expressed in degrees 2θ (+/−0.20 degree θ) at 5.3, 6.1, and 12.7 degrees 2-θ.

Form η exhibits an X-ray powder diffraction pattern having characteristic peaks expressed in degrees 2θ (+/−0.20 degree θ) at 5.3, 6.1, and 7.5 degrees 2-θ.

Form η exhibits an X-ray powder diffraction pattern having characteristic peaks expressed in degrees 2θ (+/−0.20 degree θ) at 5.3, 6.1, and 8.8 degrees 2-θ; or 6.1, 7.3, 7.5, 7.9, 8.8, and 12.7 degrees 2-θ.

Form η exhibits an X-ray powder diffraction pattern having characteristic peaks expressed in degrees 2θ (+/−0.20 degree θ) at 5.3, 6.1, 7.3, 7.5, 7.9, 8.8, 12.7 degrees 2-θ.

Form η exhibits an X-ray powder diffraction pattern having characteristic peaks expressed in degrees 2θ (+/−0.20 degree θ) at 5.3, 6.1, 7.3, 7.9, 8.8, and 12.7 degrees 2-θ.

Form η exhibits an X-ray powder diffraction pattern having characteristic peaks expressed in degrees 2θ (+/−0.20 degree θ) at 5.3, 6.1, 7.3, 7.5, 8.8, and 12.7 degrees 2-θ. Form η exhibits an X-ray powder diffraction pattern having characteristic peaks expressed in degrees 2θ (+/−0.20 degree θ) at 5.3, 6.1, 7.3, 7.5, 7.9, 8.8, and 12.7 degrees 2-θ.

Some features of polymorph Form ι, Form Iota-dry and Iota-dry' include, for example:

The polymorph Form ι exhibits an X-ray powder diffraction pattern having characteristic peaks expressed in degrees 2θ (+/−0.20 degree θ) at 5.49, 5.88, 7.86, 9.03, 12.66, and 13.89.

The polymorph Form ι exhibits an X-ray powder diffraction pattern having characteristic peaks expressed in degrees 2θ (+/−0.20 degree θ) at 5.49, 5.88, 7.86, 9.03, and 12.66.

The polymorph Form ι exhibits an X-ray powder diffraction pattern having characteristic peaks expressed in degrees 2θ (+/−0.20 degree θ) at 5.49, 5.88, 7.86, 9.03, and 13.89.

The polymorph Form ι exhibits an X-ray powder diffraction pattern having characteristic peaks expressed in degrees 2θ (+/−0.20 degree θ) at 5.49, 5.88, 9.03, 12.66, and 13.89.

The polymorph Form ι exhibits an X-ray powder diffraction pattern having characteristic peaks expressed in degrees 2θ (+/−0.20 degree θ) at 5.49, 7.86, 9.03, 12.66, and 13.89.

The polymorph Form ι exhibits an X-ray powder diffraction pattern having characteristic peaks expressed in degrees 2θ (+/−0.20 degree θ) at 5.88, 7.86, 9.03, 12.66, and 13.89.

The polymorph Form ι exhibits an X-ray powder diffraction pattern having characteristic peaks expressed in degrees 2θ (+/−0.20 degree θ) at 5.9; 7.9; 9.0; or 12.7; 13.9; 14.9; or 5.9; 7.9; 12.7; or 5.9; 9.0; 12.7; or 5.9; 13.9; 14.9; or 5.9; 7.9; 14.9; or 9.0; 12.7; 14.9; or 5.9; 7.9; 9.0; 14.9; or 5.9; 7.9; 9.0; 12.7; or 5.9; 7.9; 9.0; 12.7; 13.9; 14.9.

The polymorph Form ι exhibits an X-ray powder diffraction pattern having characteristic peaks expressed in degrees 2θ (+/−0.20 degree θ) at 5.9; 7.4; 7.9; 9.4.

The polymorph Form ι exhibits an X-ray powder diffraction pattern having characteristic peaks expressed in degrees 2θ (+/−0.20 degree θ) at 7.4; 20.0; 20.9.

The polymorph Form ι exhibits an X-ray powder diffraction pattern having characteristic peaks expressed in degrees 2θ (+/−0.20 degree θ) at 5.9; 13.9; 14.9.

The polymorph Form ι exhibits an X-ray powder diffraction pattern having characteristic peaks expressed in degrees 2θ (+/−0.20 degree θ) at 20.0; 20.9; 23.4.

The polymorph Form ι exhibits an X-ray powder diffraction pattern having characteristic peaks expressed in degrees 2θ (+/−0.20 degree θ) at 5.9; 13.9; 14.9; 20.0; 20.9.

The polymorph Form ι exhibits an X-ray powder diffraction pattern having characteristic peaks expressed in degrees 2θ (+/−0.20 degree θ) at 7.4; 12.7; 13.9; 23.4.

The polymorph Form ι exhibits an X-ray powder diffraction pattern having characteristic peaks expressed in degrees 2θ (+/−0.20 degree θ) at 5.9; 7.4; 7.9; 12.7; 13.9; 14.9; 20.0; 20.9; 23.4.

The polymorph Form ι exhibits an X-ray powder diffraction pattern having characteristic peaks expressed in degrees 2θ (+/−0.20 degree θ) at 5.9; 7.4; 7.9; 9.0; 9.4; 12.7; 13.9; 14.9; 20.0; 20.9; 23.4

The polymorph Form ι exhibits an X-ray powder diffraction pattern having characteristic peaks expressed in degrees 2θ (+/−0.20 degree θ) at 5.9; 13.9; 14.9; 20.0; 20.9; or 5.9; 13.9; 14.9; or 7.4; 12.7; 13.9; 23.4; or 20.0; 20.9; 23.4; or 5.9; 7.4; 7.9; 12.7; 13.9; 14.9; 20.0; 20.9; 23.4; or 5.9; 7.4; 7.9; 9.4; or 7.4; 20.0; 20.9; or 5.9; 7.4; 7.9; 9.0; 9.4; 12.7; 13.9; 14.9; 20.0; 20.9; 23.4.

The polymorph Form ι exhibits an X-ray powder diffraction pattern having characteristic peaks expressed in degrees 2θ (+/−0.20 degree θ) at 5.9; 7.9; 9.0; 12.7; 13.9; 14.9.

The polymorph Form ι exhibits an X-ray powder diffraction pattern having characteristic peaks expressed in degrees 2θ (+/−0.20 degree θ) at 5.9; 7.9; 9.0.

The polymorph Form ι exhibits an X-ray powder diffraction pattern having characteristic peaks expressed in degrees 2θ (+/−0.20 degree θ) at 12.7; 13.9; 14.9.

The polymorph Form ι exhibits an X-ray powder diffraction pattern having characteristic peaks expressed in degrees 2θ (+/−0.20 degree θ) at 5.9; 7.9; 12.7.

The polymorph Form ι exhibits an X-ray powder diffraction pattern having characteristic peaks expressed in degrees 2θ (+/−0.20 degree θ) at 5.9; 9.0; 12.7.

The polymorph Form ι exhibits an X-ray powder diffraction pattern having characteristic peaks expressed in degrees 2θ (+/−0.20 degree θ) at 5.9; 13.9; 14.9.

The polymorph Form ι-dry exhibits an X-ray powder diffraction pattern having characteristic peaks expressed in degrees 2θ (+/−0.20 degree θ) at 6.04, 7.90, 8.92, 9.49, 12.76, and 14.14.

The polymorph Form ι-dry exhibits an X-ray powder diffraction pattern having characteristic peaks expressed in degrees 2θ (+/−0.20 degree θ) at 7.90, 8.92, 9.49, 12.76, and 14.14.

The polymorph Form ι-dry exhibits an X-ray powder diffraction pattern having characteristic peaks expressed in degrees 2θ (+/−0.20 degree θ) at 6.04, 8.92, 9.49, 12.76, and 14.14.

The polymorph Form ι-dry exhibits an X-ray powder diffraction pattern having characteristic peaks expressed in degrees 2θ (+/−0.20 degree θ) at 6.04, 7.90, 9.49, 12.76, and 14.14.

The polymorph Form ι-dry exhibits an X-ray powder diffraction pattern having characteristic peaks expressed in degrees 2θ (+/−0.20 degree θ) at 6.04, 7.90, 8.92, 12.76, and 14.14.

The polymorph Form ι-dry exhibits an X-ray powder diffraction pattern having characteristic peaks expressed in degrees 2θ (+/−0.20 degree θ) at 6.04, 7.90, 8.92, 9.49, and 14.14.

The polymorph Form ι-dry exhibits an X-ray powder diffraction pattern having characteristic peaks expressed in degrees 2θ (+/−0.20 degree θ) at 6.04, 7.90, 8.92, 9.49, and 12.76.

The polymorph Form ι-dry' exhibits an X-ray powder diffraction pattern having characteristic peaks expressed in degrees 2θ (+/−0.20 degree θ) at 6.16, 7.92, 8.89, 9.55, 12.80, and 14.25.

The polymorph Form ι-dry' exhibits an X-ray powder diffraction pattern having characteristic peaks expressed in degrees 2θ (+/−0.20 degree θ) at 7.92, 8.89, 9.55, 12.80, and 14.25.

The polymorph Form ι-dry' exhibits an X-ray powder diffraction pattern having characteristic peaks expressed in degrees 2θ (+/−0.20 degree θ) at 6.16, 8.89, 9.55, 12.80, and 14.25.

The polymorph Form ι-dry' exhibits an X-ray powder diffraction pattern having characteristic peaks expressed in degrees 2θ (+/−0.20 degree θ) at 6.16, 7.92, 9.55, 12.80, and 14.25.

The polymorph Form ι-dry' exhibits an X-ray powder diffraction pattern having characteristic peaks expressed in degrees 2θ (+/−0.20 degree θ) at 6.16, 7.92, 8.89, 12.80, and 14.25.

The polymorph Form ι-dry' exhibits an X-ray powder diffraction pattern having characteristic peaks expressed in degrees 2θ (+/−0.20 degree θ) at 6.16, 7.92, 8.89, 9.55, and 14.25

The polymorph Form ι-dry' exhibits an X-ray powder diffraction pattern having characteristic peaks expressed in degrees 2θ (+/−0.20 degree θ) at 6.16, 7.92, 8.89, 9.55, and 12.80.

Some features of polymorph Form B include, for example:

The polymorph Form B exhibits an X-ray powder diffraction pattern having characteristic peaks expressed in degrees 2θ (+/−0.20 degree θ) at 5.24, 6.84, 7.74, 8.71, 10.16, and 12.21.

The polymorph Form B exhibits an X-ray powder diffraction pattern having characteristic peaks expressed in degrees 2θ (+/−0.20 degree θ) at 6.84, 7.74, 8.71, 10.16, and 12.21.

The polymorph Form B exhibits an X-ray powder diffraction pattern having characteristic peaks expressed in degrees 2θ (+/−0.20 degree θ) at 5.24, 7.74, 8.71, 10.16, and 12.21.

The polymorph Form B exhibits an X-ray powder diffraction pattern having characteristic peaks expressed in degrees 2θ (+/−0.20 degree θ) at 5.24, 6.84, 8.71, 10.16, and 12.21.

The polymorph Form B exhibits an X-ray powder diffraction pattern having characteristic peaks expressed in degrees 2θ (+/−0.20 degree θ) at 5.24, 6.84, 7.74, 10.16, and 12.21.

The polymorph Form B exhibits an X-ray powder diffraction pattern having characteristic peaks expressed in degrees 2θ (+/−0.20 degree θ) at 5.24, 6.84, 7.74, 8.71, and 12.21.

The polymorph Form B exhibits an X-ray powder diffraction pattern having characteristic peaks expressed in degrees 2θ (+/−0.20 degree θ) at 5.24, 6.84, 7.74, 8.71, and 10.16.

The polymorph Form B exhibits an X-ray powder diffraction pattern having characteristic peaks expressed in degrees 2θ (+/−0.20 degree θ) at 5.24, 6.84, and 7.74.

In one embodiment, the Form ζ, Form η, Form ι, Form ι-dry, Form ι-dry', or Form B, of rifaximin contain less than 5% by weight total impurities.

In one embodiment, the Form ζ, Form η, Form ι, Form ι-dry, Form ι-dry', or Form B, of rifaximin contain less than 50% by weight total impurities.

In one embodiment, the Form ζ, Form η, Form ι, Form ι-dry, Form ι-dry', or Form B, of rifaximin contain less than 20% by weight total impurities.

In one embodiment, the Form ζ, Form η, Form ι, Form ι-dry, Form ι-dry', or Form B of rifaximin is at least 50% pure, or at least 75% pure, or at least 80% pure, or at least 90% pure, or at least 95% pure, or at least 98% pure.

According to one embodiment, the pharmaceutical composition comprises one or more of a Form ζ, Form η, Form ι, Form ι-dry, Form ι-dry', or Form B of rifaximin and a pharmaceutically acceptable carrier.

In one embodiment, the composition further comprises one or more pharmaceutically acceptable excipients. The excipients may be one or more of a diluting agent, binding agent, lubricating agent, disintegrating agent, coloring agent, flavoring agent or sweetening agent.

According to one embodiment, the pharmaceutical composition may be formulated as coated or uncoated tablets, hard or soft gelatin capsules, sugar-coated pills, lozenges, wafer sheets, pellets or powders in a sealed packet. In a related embodiment, the pharmaceutical composition may also be formulated for topical use.

According to another aspect, provided herein are methods of treating, preventing or alleviating a bowel related disorder comprising administering to a subject in need thereof an effective amount of one or more of Form ζ, Form η, Form ι, Form ι-dry, Form ι-dry', and Form B of rifaximin.

In one embodiment, the subject is suffering from at least one bowel related disorder selected from the group consisting of irritable bowel syndrome, travelers' diarrhea, small intestinal bacterial overgrowth, Crohn's disease, chronic pancreatitis, pancreatic insufficiency, enteritis and colitis.

Provided herein, according to one aspect, are packaged compositions comprising, a therapeutically effective amount of one or more of a Form ζ, Form η, Form ι, Form ι-dry, Form ι-dry', and Form B of rifaximin and a pharmaceutically acceptable carrier or diluent, wherein the composition is formulated for treating a subject suffering from or susceptible to a bowel disorder, and packaged with instructions to treat a subject suffering from or susceptible to a bowel disorder.

In one aspect, a pharmaceutical composition is presented, which comprises one or more of Form ζ, Form η, Form ι, Form ι-dry, Form ι-dry', and Form B of rifaximin and a pharmaceutically acceptable carrier.

In one aspect, a pharmaceutical composition is presented, which comprises one or more of Form ζ, Form η, Form ι, Form ι-dry, Form ι-dry', or Form B and one or more of these forms with one or more of Form alpha, Form beta, Form gamma, Form delta, or Form epsilon, of rifaximin and a pharmaceutically acceptable carrier.

In one embodiment, the pharmaceutical composition further comprises excipients.

According to another embodiment, the excipients are one or more of a diluting agent, binding agent, lubricating agent, disintegrating agent, coloring agent, flavoring agent or sweetening agent.

In another embodiment, the composition is formulated for selected coated and uncoated tablets, hard and soft gelatin capsules, sugar-coated pills, lozenges, wafer sheets, pellets and powders in sealed packets.

In one embodiment, the composition is formulated for topical use.

Presented herein, according to one aspect, are methods of treating, preventing, or alleviating a bowel related disorder comprising administering to a subject in need thereof a cell infected with a virus with an effective amount of one or more of a Form ζ, Form η, Form ι, Form ι-dry, Form ι-dry', and Form B of rifaximin.

According to another embodiment, wherein the bowel related disorder is one or more of irritable bowel syndrome, travelers' diarrhea, small intestinal bacterial overgrowth, Crohn's disease, chronic pancreatitis, pancreatic insufficiency, or colitis.

Presented herein, according to one aspect, are methods of assessing the efficacy of a bowel related disorder treatment in a subject, monitoring the progress of a subject being treated for a bowel related disorder, or a method of selecting a subject for treatment of a bowel disorder, comprising:

determining a pre-treatment level of bacterial overgrowth;

administering a therapeutically effective amount of one or more of a Form ζ, Form η, Form ι, Form ι-dry, Form ι-dry', and Form B of rifaximin to the subject; and determining a post-treatment level of bacterial overgrowth after an initial period of treatment with the one or more of Form ζ, Form η, Form ι, Form ι-dry, Form ι-dry', and Form B of rifaximin.

In one embodiment, the modulation of the level of bacterial overgrowth indicates efficacy of the treatment.

In another embodiment, a decrease in bacterial overgrowth indicates that the treatment is efficacious.

In another embodiment, the modulation of the bacterial overgrowth is an indication that the subject is likely to have a favorable clinical response to the treatment.

Presented herein, according to one aspect, are kits for treating a bowel disorder in a subject, comprising one or more actions for use.

Also presented herein, according to one aspect are packaged compositions comprising a therapeutically effective amount of one or more of a Form ζ, Form η, Form ι, Form ι-dry, Form ι-dry', and Form B of rifaximin and a pharmaceutically acceptable carrier or diluents, wherein the composition is formulated for treating a subject suffering from or susceptible to a bowel disorder, and packaged with instructions to treat a subject suffering from or susceptible to a bowel disorder.

Presented herein, is use of Form of rifaximin as a medicament.

Also presented herein is the use of Form η of rifaximin as a medicament.

Also presented herein is the use of Form ι of rifaximin as a medicament.

Also presented herein is the use of Form ι-dry of rifaximin as a medicament.

Also presented herein is the use of Form ι-dry' of rifaximin as a medicament.

Also presented herein is the use of Form B of rifaximin as a medicament.

Presented herein, according to another aspect, are processes for the production of one or more of a Form ζ, Form η, Form ι, Form ι-dry, Form ι-dry', and Form B of rifaximin.

Methods of Treatment

Provided herein are methods of treating, preventing, or alleviating bowel related disorders comprising administering to a subject in need thereof an effective amount of one or more of the Forms of rifaximin described herein. Bowel related disorders include one or more of irritable bowel syndrome, diarrhea, microbe associated diarrhea, *Clostridium difficile* associated diarrhea, travelers' diarrhea, small intestinal bacterial overgrowth, Crohn's disease, chronic pancreatitis, pancreatic insufficiency, enteritis, colitis, hepatic encephalopathy, or pouchitis.

The length of treatment for a particular bowel disorder will depend in part on the disorder. For example, travelers' diarrhea may only require treatment duration of 12 to about 72 hours, while Crohn's disease may require treatment durations from about 2 days to 3 months. Dosages of rifaximin will also vary depending on the diseases state. Proper dosage ranges are provided herein infra.

Provided herein are methods of treating or preventing a pathology in a subject suspected of being exposed to a biological warfare agent.

The identification of those subjects who are in need of prophylactic treatment for bowel disorder is well within the ability and knowledge of one skilled in the art. Certain of the methods for identification of subjects which are at risk of developing a bowel disorder which can be treated by the subject method are appreciated in the medical arts, such as family history, travel history and expected travel plans, the presence of risk factors associated with the development of that disease state in the subject. A clinician skilled in the art can readily identify such candidate subjects, by the use of, for example, clinical tests, physical examination and medical/family/travel history.

A method of assessing the efficacy of the treatment in a subject includes determining the pre-treatment level of intestinal bacterial overgrowth by methods well known in the art (e.g., hydrogen breath testing, biopsy, sampling of the intestinal bacteria, etc.) and then administering a therapeutically effective amount of a rifaximin polymorph to the subject. After an appropriate period of time (e.g., after an initial period of treatment) from the administration of the compound, e.g., 2 hours, 4 hours, 8 hours, 12 hours, or 72 hours, the level of bacterial overgrowth is determined again. The modulation of the bacterial level indicates efficacy of the treatment. The level of bacterial overgrowth may be determined periodically throughout treatment. For example, the bacterial overgrowth may be checked every few hours, days or weeks to assess the further efficacy of the treatment. A decrease in bacterial overgrowth indicates that the treatment is efficacious. The method described may be used to screen or select subjects that may benefit from treatment with a rifaximin polymorph.

In yet another aspect, a method of treating a subject suffering from or susceptible to a bowel disorder comprises administering to a subject in need thereof a therapeutically effective amount of a rifaximin polymorph described herein, to thereby treat the subject. Upon identification of a subject suffering from or susceptible to a bowel disorder, for example, IBS, one or more rifaximin polymorphs are administered.

In one aspect, methods of assessing the efficacy of treatment with a rifaximin polymorph in a subject comprise determining the pre-treatment level of bacterial overgrowth, administering a therapeutically effective amount of a rifaximin polymorph to the subject, and determining the bacterial overgrowth after an initial period of treatment with a rifaximin polymorph, wherein the modulation of the bacterial overgrowth indicates efficacy of an anti-bacterial treatment.

Efficacy of a treatment may be measured for example, as reduction of bacterial overgrowth. Efficacy may also be measured in terms of a reduction of symptoms associated with the bowel disorder, a stabilization of symptoms, or a cessation of symptoms associated with a bowel disorder, for example, a reduction of nausea, bloating, diarrhea, and the like.

In one aspect, methods of monitoring the progress of a subject being treated with a rifaximin polymorph comprise determining the pre-treatment level of bacterial overgrowth, administering a therapeutically effective amount of a rifaximin polymorph to the subject, and determining the bacterial overgrowth after an initial period of treatment with a rifaximin polymorph, wherein the modulation of the bacterial overgrowth indicates efficacy of an anti-bacterial treatment.

Pharmaceutical Preparations

Embodiments also provide pharmaceutical compositions, comprising an effective amount of a rifaximin polymorph (e.g., Form ζ, Form η, Form ι, Form ι-dry, Form ι-dry', and Form B) described herein and a pharmaceutically acceptable carrier. In a further embodiment, the effective amount is effective to treat a bacterial infection, e.g., small intestinal bacterial overgrowth, Crohn's disease, hepatic encephalopathy, antibiotic associated colitis, and/or diverticular disease.

For examples of the use of rifaximin to treat Travelers' diarrhea, see Infante R M, Ericsson C D, Zhi-Dong J, Ke S, Steffen R, Riopel L, Sack D A, DuPont, H L. Enteroaggregative *Escherichia coli* Diarrhea in Travelers: Response to Rifaximin Therapy. *Clinical Gastroenterology and Hepatology.* 2004; 2:135-138; and Steffen R, M.D., Sack D A, M.D., Riopel L, Ph.D., Zhi-Dong J, Ph.D., Sturchler M, M.D., Ericsson C D, M.D., Lowe B, M. Phil., Waiyaki P, Ph.D., White M, Ph.D., DuPont H L, M.D. Therapy of Travelers' Diarrhea With Rifaximin on Various Continents. *The American Journal of Gastroenterology.* May 2003, Volume 98, Number 5, all of which are incorporated herein by reference in their entirety.

Embodiments also provide pharmaceutical compositions comprising one or more of a Form ζ, Form η, Form ι, Form ι-dry, Form ι-dry', and Form B of rifaximin and a pharmaceutically acceptable carrier. That is, formulations may contain only one polymorph or may contain a mixture of more than one polymorph. Mixtures may be selected, for example on the basis of desired amounts of systemic adsorption, dissolution profile, desired location in the digestive tract to be treated, and the like. Embodiments of the pharmaceutical composition further comprise excipients, for example, one or more of a diluting agent, binding agent, lubricating agent, disintegrating agent, coloring agent, flavoring agent or sweetening agent. One composition may be formulated for selected coated and uncoated tablets, hard and soft gelatin capsules, sugar-coated pills, lozenges, wafer sheets, pellets and powders in sealed packet. For example, compositions may be formulated for topical use, for example, ointments, pomades, creams, gels and lotions.

In an embodiment, the rifaximin polymorph is administered to the subject using a pharmaceutically-acceptable formulation, e.g., a pharmaceutically-acceptable formulation that provides sustained delivery of the rifaximin polymorph to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those rifaximin polymorphs of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is preferably "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a rifaximin forms disclosed herein include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred %, this amount will range from about 1% to about ninety-nine % of active ingredient, preferably from about 5% to about 70%, most preferably from about 10% to about 30%.

Methods of preparing these compositions include the step of bringing into association a rifaximin polymorph(s) with the carrier and, optionally, one or more accessory ingredients. In general, the formulations are prepared by uniformly and intimately bringing into association a rifaximin polymorph with liquid carriers, or finely divided solid carriers, or both, and then, if necessary, shaping the product.

Compositions suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a rifaximin polymorph(s) as an active ingredient. A compound may also be administered as a bolus, electuary or paste.

The Forms disclosed herein can be advantageously used in the production of medicinal preparations having antibiotic activity, containing rifaximin, for both oral and topical use. The medicinal preparations for oral use will contain rifaximin Forms disclosed herein together with the usual excipients, for example diluting agents such as mannitol, lactose and sorbitol; binding agents such as starches, gelatines, sugars, cellulose derivatives, natural gums and polyvinylpyrrolidone; lubricating agents such as talc, stearates, hydrogenated vegetable oils, polyethylenglycol and colloidal silicon dioxide; disintegrating agents such as starches, celluloses, alginates, gums and reticulated polymers; colouring, flavouring and sweetening agents.

Embodiments of the invention include solid preparations administrable by the oral route, for instance coated and uncoated tablets, of soft and hard gelatin capsules, sugar-coated pills, lozenges, wafer sheets, pellets and powders in sealed packets or other containers.

Medicinal preparations for topical use can contain rifaximin Forms described herein or other previously described Forms of rifaximin together with usual excipients, such as white petrolatum, white wax, lanoline and derivatives thereof, stearylic alcohol, propylene glycol, sodium lauryl sulfate, ethers of fatty polyoxyethylene alcohols, esters of fatty polyoxyethylene acids, sorbitan monostearate, glyceryl monostearate, propylene glycol monostearate, polyethylene glycols, methylcellulose, hydroxymethyl propylcellulose, sodium carboxymethylcellulose, colloidal aluminium and magnesium silicate, sodium alginate.

Embodiments of the invention relate to all of the topical preparations, for instance ointments, pomades, creams, gels and lotions.

In solid dosage forms of rifaximin for oral administration (capsules, tablets, pills, dragees, powders, granules and the like), the active ingredient is typically mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) colouring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions described herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the rifaximin polymorph(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active rifaximin polymorph(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions for rectal or vaginal administration may be presented as a suppository, which may be prepared by mixing one or more rifaximin polymorph(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions which are suitable for vaginal administration also include pessaries, tampons, creams, gels, pastes, foams or spray formulations containing such carriers as are known in the art to be appropriate.

Dosage forms for the topical or transdermal administration of a rifaximin polymorph(s) include powders, sprays, ointments, pastes, creams, lotions, gels, solutions, patches and inhalants. The active rifaximin polymorph(s) may be mixed under sterile conditions with a pharmaceutically-acceptable carrier, and with any preservatives, buffers, or propellants which may be required.

Ointments, pastes, creams and gels may contain, in addition to rifaximin polymorph(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a rifaximin polymorph(s), excipients such as lactose, talc, silicic acid, aluminium hydroxide, calcium silicates and polyamide powder, or mixtures of these substances. Sprays can additionally contain customary propellants, such as chlorofluorohydrocarbons and volatile unsubstituted hydrocarbons, such as butane and propane.

The rifaximin polymorph(s) can be alternatively administered by aerosol. This is accomplished by preparing an aqueous aerosol, liposomal preparation or solid particles containing the compound. A non-aqueous (e.g., fluorocarbon propellant) suspension could be used. Sonic nebulizers are preferred because they minimize exposing the agent to shear, which can result in degradation of the compound.

An aqueous aerosol is made, for example, by formulating an aqueous solution or suspension of the agent together with conventional pharmaceutically-acceptable carriers and stabilizers. The carriers and stabilizers vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a rifaximin polymorph(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions suitable for parenteral administration may comprise one or more rifaximin polymorph(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, to prolong the effect of a drug, it is desirable to alter the absorption of the drug. This may be accomplished by the use of a liquid suspension of crystalline, salt or amorphous material having poor water solubility. The rate of absorption of the drug may then depend on its rate of dissolution which, in turn, may depend on crystal size and crystalline form. Alternatively, delayed absorption of a drug form is accomplished by dissolving or suspending the drug in an oil vehicle.

Injectable depot forms are made by forming microencapsule matrices of rifaximin polymorph(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the rifaximin polymorph(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the rifaximin polymorph(s), which may be used in a suitable hydrated form, and/or the pharmaceutical compositions of the present invention, are formulated into pharmaceutically-acceptable dosage forms by methods known to those of skill in the art.

Actual dosage levels and time course of administration of the active ingredients in the pharmaceutical compositions may be varied so as to obtain an amount of the active ingredient which is effective to achieve the desired therapeutic response for a particular subject, composition, and mode of administration, without being toxic to the subject. An exemplary dose range is from 25 to 3000 mg per day.

A preferred dose of the rifaximin polymorph for the present invention is the maximum that a subject can tolerate without developing serious side effects. Preferably, the rifaximin polymorph of the present invention is administered at a concentration of about 1 mg to about 200 mg per kilogram of body weight, about 10-about 100 mg/kg or about 40 mg-about 80 mg/kg of body weight. Ranges intermediate to the above-recited values are also intended to be part.

In combination therapy treatment, both the compounds of this invention and the other drug agent(s) are administered to mammals (e.g., humans, male or female) by conventional methods. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment in which another therapeutic agent is administered to an animal, the effective amount of the compound of this invention is less than its effective amount in case the other therapeutic agent is not administered. In another embodiment, the effective amount of the conventional agent is less than its effective amount in case the compound of this invention is not administered. In this way, undesired side effects associated with high doses of either agent may be minimized. Other potential advantages (including without limitation improved dosing regimens and/or reduced drug cost) will be apparent to those skilled in the art.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same subject's visit.

In certain embodiments, one or more compounds and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the administration of the same compounds may be repeated and the administrations may be separated by at least 1 day, 2 days, 3 days, 5 days, 10 days, 15 days, 30 days, 45 days, 2 months, 75 days, 3 months, or at least 6 months. In other embodiments, the administration of the same therapy (e.g., prophylactic or therapeutic agent) other than a rifaximin polymorph may be repeated and the administration may be separated by at least 1 day, 2 days, 3 days, 5 days, 10 days, 15 days, 30 days, 45 days, 2 months, 75 days, 3 months, or at least 6 months.

Certain indications may require longer treatment times. For example, travelers' diarrhea treatment may only last from between about 12 hours to about 72 hours, while a treatment for Crohn's disease may be from between about 1 day to about 3 months. A treatment for hepatic encephalopathy may be, for example, for the remainder of the subject's life span. A treatment for IBS may be intermittent for weeks or months at a time or for the remainder of the subject's life.

Article of Manufacture

Another embodiment includes articles of manufacture that comprise, for example, a container holding a pharmaceutical composition suitable for oral or topical administration of rifaximin in combination with printed labeling instructions providing a discussion of when a particular dosage form should be administered with food and when it should be taken on an empty stomach. Exemplary dosage forms and administration protocols are described infra. The composition will be contained in any suitable container capable of holding and dispensing the dosage form and which will not significantly interact with the composition and will further be in physical relation with the appropriate labeling. The labeling instructions will be consistent with the methods of treatment as described hereinbefore. The labeling may be associated with the container by any means that maintain a physical proximity of the two, by way of non-limiting example, they may both be contained in a packaging material such as a box or plastic shrink wrap or may be associated with the instructions being bonded to the container such as with glue that does not obscure the labeling instructions or other bonding or holding means.

Another aspect is an article of manufacture that comprises a container containing a pharmaceutical composition comprising rifaximin wherein the container holds preferably rifaximin composition in unit dosage form and is associated with printed labeling instructions advising of the differing absorption when the pharmaceutical composition is taken with and without food.

Packaged compositions are also provided, and may comprise a therapeutically effective amount of rifaximin. Rifaximin and a pharmaceutically acceptable carrier or diluent, wherein the composition is formulated for treating a subject suffering from or susceptible to a bowel disorder, and packaged with instructions to treat a subject suffering from or susceptible to a bowel disorder.

Kits are also provided herein, for example, kits for treating a bowel disorder in a subject. The kits may contain, for example, one or more of a Form of rifaximin and instructions for use. The instructions for use may contain proscribing information, dosage information, storage information, and the like.

Packaged compositions are also provided, and may comprise a therapeutically effective amount of one or more of a polymorph of rifaximin and a pharmaceutically acceptable carrier or diluent, wherein the composition is formulated for treating a subject suffering from or susceptible to a bowel disorder, and packaged with instructions to treat a subject suffering from or susceptible to a bowel disorder.

EXAMPLES

Characterization of Forms

Some of the hydrated, salt and amorphous forms of rifaximin, were characterized by one or more of XRPD, thermal analysis, FT-IR, FT-Raman, $^{13}$C NMR. Dried materials obtained by vacuum drying or heating the hydrates were labeled "dry". These materials exhibited XRPD patterns that were shifted or contained one or two additional small peaks when compared to the undried material.

X-ray powder diffraction (XRPD)

X-ray powder diffraction (XRPD) analyses were performed using an Inel XRG-3000 diffractometer equipped with a CPS (Curved Position Sensitive) detector with a 2θ range of 120°. Real time data were collected using Cu-Kα radiation starting at approximately 4°2θ at a resolution of 0.03°2θ. The tube voltage and amperage were set to 40 kV and 30 mA, respectively. The monochromator slit was set at 5 mm by 160 μm. The pattern is displayed from 2.5-40°2θ. Samples were prepared for analysis by packing them into thin-walled glass capillaries. Each capillary was mounted onto a goniometer head that is motorized to permit spinning of the capillary during data acquisition. The samples were analyzed for 300 seconds. Instrument calibration was performed using a silicon reference standard. The experimental XRPD pattern was collected at SSCI, Inc. according to cGMP specifications.

Methods of Preparation

Methods of Preparation for Rifaximin Form Iota-Dry (ι-Dry)

Rifaximin (0.0960 g) was combined with methanol (300 μL) resulting in a clear red solution. The vial was capped and left at ambient conditions. After one day, a red precipitate consisting of birefringent blades and needles were noted by optical microscopy. After two days, the whole of solution was noted as crystallized. The damp crystals were stored refrigerated (2-8° C.) for one day prior to XRPD analysis. XRPD analysis indicated Form ζ.

After one month of refrigerated storage, single crystal structure determination of one crystal was identified as rifaximin Form ι-dry. The bulk sample was not analyzed by XRPD.

Rifaximin (Form ι, quantity unmeasured) was placed in a clean vial and covered with perforated aluminum foil. The vial was then placed in a vacuum oven set at 23° C. at ~30 mm Hg. After 15 hours the sample was removed from the vacuum oven, the vial capped and submitted for XRPD analysis.

Rifaximin (Form ι) was placed in a vial covered with perforated aluminum foil. The vial was then placed in a vacuum oven set at 22° C. and ~30 mmHg. After ~16 hours the sample was removed from the vacuum oven and submitted for XRPD analysis.

Rifaximin (7.7 mg) was subjected to dynamic vapor sorption/desorption analysis. The sample was not dried prior to analysis. Adsorption and desorption data were collected over a range from 5 to 95% RH at 10% RH increments under a nitrogen purge. The equilibrium criterion used for analysis was less than 0.0100% weight change in 5 minutes with a maximum equilibration time of 3 hours. After analysis, the sample was placed in a clean vial and submitted for XRPD analysis.

FT-IR analysis of the sample was also conducted 4 months later. The sample was not re-analyzed by XRPD to confirm the form.

Rifaximin (Form ι-dry, quantity unmeasured) was placed in a vacuum oven set at 23° C. and 8-30 in Hg for 3 days. The sample was packed in a glass capillary and submitted for XRPD.

Rifaximin (quantity unmeasured) was placed in a vacuum oven set at 23° C. and 8-30 in Hg for 3 days. The sample was packed in a glass capillary and submitted for XRPD. Form ι-dry showed approximately 4.2% weight loss from 35-115° C. by TG. The weight loss corresponds with a broad endotherm at approximately 57° C. in the DSC, likely indicative of solvent loss. An additional endotherm at approximately 204° C. in the DSC thermogram is ascribed to a melt. Proton NMR spectrum showed no presence of organic solvent in the proton spectrum of Form ι-dry.

Rifaximin (quantity unmeasured) was placed in a clean vial. The vial was covered with perforated aluminum foil and placed in a vacuum oven set at 23° C. and 8-30 in Hg. After approximately 15 hours, the sample was removed from the vacuum oven and submitted for XRPD analysis.

After 3 months and 1 week of storage at ambient conditions, the sample was submitted for XRPD analysis.

Rifaximin (quantity unmeasured) was placed in a clean vial and allowed to air-dry at ambient conditions. After approximately 3 hours the sample appeared dry by perturbation with a spatula and was submitted for XRPD analysis. The sample was stored at ambient conditions for approximately 4 months and again analyzed by XRPD.

Form ι-dry was exposed to ethanol vapor at an initial relative vapor pressure of 0.45 decreasing to 0.05 in 0.1 increments. The material demonstrated a percent weight gain of approximately 10.3% after 10 minutes at 0.45 relative vapor pressure, equivalent to two moles of ethanol. The material lost 1.47% of the gained weight (approximately 0.25 mole ethanol) on the desorption curve from 0.45 to 0.05 relative pressure over 33 minutes. XRPD analysis of the sample after DVS analysis showed a form eta.

Form ι-dry was exposed to ethanol vapor with a one step for saturation at 0.45 relative pressure of ethanol. The material demonstrated a 10.3% weight gain (equivalent to 2 moles of ethanol). XRPD analysis of the sample after DVS analysis showed Form ι.

Rifaximin (150 μL) was placed in a clean vial and placed in the freezer (−10 to −25° C.). After 57 days wet, birefringent red orange blades were noted as individual crystals and spherulites and submitted for XRPD analysis.

Rifaximin (quantity unmeasured, both in capillary and bulk) was placed in a jar containing a saturated salt solution to maintain a relative humidity of 97% RH (saturated salt solution of potassium sulfate in water). After 38 days the sample was analyzed by XRPD.

Methods of Preparation for Rifaximin Form Iota (ι)

Rifaximin (0.0294 g) was dissolved in ethanol (100 μL) resulting in a clear red solution. A red precipitate spontaneously occurred in less than 5 minutes. The vial was capped and left at ambient conditions. Wet red-orange birefringent fine needles were packed in a capillary and submitted for XRPD analysis. The remainder of the sample was allowed to air-dry. After less than one hour, the material appeared dry. Fine red-orange needles exhibiting partial birefringence were submitted for XRPD.

Rifaximin (0.0996 g) was dissolved in methanol (300 μL) with sonication resulting in a clear red solution. A portion of the solution (150 μL) was removed for another experiment. The vial was then capped and refrigerated (2-8° C.) for 3 days. A clear red solution was noted and the sample was transferred to the freezer (−10 to −25° C.). Wet, birefringent orange-red solids with dendritic formations were noted after 20 days. The sample was transferred to the refrigerator (2-8° C.) and submitted for XRPD.

Sample was analyzed by DSC, TGA, DVS, 1H NMR, FT-IR and hotstage microscopy approximately one month later.

Rifaximin (Form ζ (not refined), quantity unmeasured) was transferred to a clean vial and allowed to air-dry at ambient conditions. After approximately 3 hours the sample appeared dry by touch with a spatula and was submitted for XRPD analysis.

Form ι dry was exposed to ethanol vapor with a one step for saturation at 0.45 relative pressure of ethanol. The material demonstrated a 10.3% weight gain (equivalent to 2 moles of ethanol). XRPD analysis of the sample after DVS analysis showed Form ι.

Rifaximin (Form ζ, quantity unmeasured) was transferred to a clean vial and allowed to air-dry at ambient conditions. After approximately 3 hours the sample appeared dry by touch with a spatula and was submitted for XRPD analysis.

Rifaximin (0.1004 g) was dissolved in ethanol (340 μL) using a vortex mixer and spatula. A dark red solution was obtained and yielded an orange red precipitate after 5 min. Tiny birefringent needles were submitted wet for XRPD analysis. Form ζ on first analysis Form eta upon re-analysis. The sample was analyzed again after 3 months and 7 days of storage at ambient conditions.

Rifaximin (0.0284 g) was dissolved in ethanol (100 μL) resulting in a clear red solution (Nov. 7, 2008). A red precipitate spontaneously occurred in less than 5 minutes. The vial was capped and left at ambient conditions. Wet red-orange birefringent fine needles were packed in a capillary and submitted for XRPD analysis. The remainder of the sample was allowed to air-dry. After less than one hour, the material appeared dry. Fine red-orange needles exhibiting partial birefringence were submitted for XRPD.

Rifaximin (0.0996 g) was dissolved in methanol (300 μL) with sonication resulting in a clear red solution. A portion of the solution (150 μL) was removed for another experiment. The vial was then capped and refrigerated (2-8° C.) for 3 days. A clear red solution was noted and the sample was transferred to the freezer (−10 to −25° C.). Wet, birefringent orange-red solids with dendritic formations were noted after 20 days. The sample was transferred to the refrigerator (2-8° C.) and submitted for XRPD.

Rifaximin (0.1004 g) was dissolved in ethanol (340 μL) using a vortex mixer and spatula. A dark red solution was obtained and yielded an orange red precipitate after 5 min. Tiny birefringent needles were submitted wet for XRPD analysis. The sample was analyzed again after 3 months and 7 days of storage at ambient conditions (a form eta). This sample was Form on first analysis and then Form eta upon re-analysis.

Rifaximin (0.0996 g) was dissolved in methanol (300 μL) with sonication resulting in a clear red solution. A portion of the solution (150 μL) was removed for another experiment. The vial was then capped and refrigerated (2-8° C.) for 3 days. A clear red solution was noted and the sample was transferred to the freezer (−10 to −25° C.). Wet, birefringent orange-red solids with dendritic formations were noted after 20 days. The sample was transferred to the refrigerator (2-8° C.) and submitted for XRPD.

Rifaximin (0.0996 g) was dissolved in methanol (300 μL) with sonication resulting in a clear red solution. A portion of the solution (150 μL) was removed for another experiment. The vial was then capped and refrigerated (2-8° C.) for 3 days. A clear red solution was noted and the sample was transferred to the freezer (−10 to −25° C.). Wet, birefringent orange-red solids with dendritic formations were noted after 20 days. The sample was transferred to the refrigerator (2-8° C.) and submitted for XRPD.

Methods of Preparation for Rifaximin Form Eta

Rifaximin (0.1004 g) was dissolved in ethanol (340 μL) using a vortex mixer and spatula. A dark red solution was obtained and yielded an orange red precipitate after 5 min. Tiny birefringent needles were submitted wet for XRPD analysis. Form on first analysis Form eta upon re-analysis. The sample was analyzed again after 3 months and 7 days of storage at ambient conditions.

Methods of Preparation for Rifaximin Form Zeta (ζ)

Rifaximin (265 mg) was combined with ethanol (1 mL) with shaking and sonication. The sample was slurried at ambient temperature on a shaker block for 3 days. Solvent was removed by decantation and orange fragments exhibiting birefringence and extinction were analyzed damp by XRPD.

Rifaximin (200 mg) was combined with ethanol (1 mL) and water (20 μL) with shaking and sonication. The sample was slurried at ambient temperature on a shaker block for 3 days. Solvent was removed by decantation and orange irregular fragments exhibiting birefringence and extinction were analyzed damp by XRPD.

Rifaximin (256 mg) was combined with ethanol (1 mL) and water (100 μL) with shaking and sonication. The sample was slurried at ambient temperature on a shaker block for 3 days. Solvent was removed by decantation and orange irregular fragments exhibiting birefringence and extinction were stored refrigerated (2-8° C.) and analyzed damp by XRPD.

Rifaximin (256 mg) was combined with ethanol (1 mL) and water (100 μL) with shaking and sonication. The sample was slurried at ambient temperature on a shaker block for 3 days. Solvent was removed by decantation and orange irregular fragments exhibiting birefringence and extinction were stored refrigerated (2-8° C.) and analyzed damp by XRPD. After 3 weeks refrigerated storage the sample was analyzed by XRPD.

Rifaximin (353 mg) was combined with ethanol (1 mL) and water (0.25 mL) with shaking and sonication. The sample was heated on a hot plate (set temperature 68° C.) resulting in a clear orange solution. Heating was discontinued and the vial allowed to cool to ambient temperature on the hot plate. After 3 days the clear solution was placed in the refrigerator (2-8° C.). A clear solution was noted after 2 days and the sample seeded with rifaximin. One day later orange needles exhibiting birefringence and extinction were collected by filtration. The filter cake was submitted for XRPD analysis without further drying.

Rifaximin (130 mg) was combined with ethanol (4 mL) with shaking. The resulting clear solution was filtered through a 0.2 μm nylon filter. The solvent was allowed to evaporate slowly. Six days later orange needles exhibiting birefringence and extinction were collected by filtration. The filter cake was submitted for XRPD analysis without further drying.

Rifaximin (404.5 mg) was combined with ethanol (2.0 mL) and water (0.5 mL). The vial was capped and the damp solids placed in the refrigerator (2-8° C.). Solids were analyzed damp by XRPD.

Rifaximin (0.0960 g) was combined with methanol (300 μL) with sonication. The resulting clear solution was capped and left at ambient temperature. A red precipitate consisting of birefringent blades and needles was observed after one day. After an additional day, the entire solution crystallized and damp crystals were noted. The sample was stored refrigerated.

Rifaximin (0.1004 g) was dissolved in ethanol (340 μL) using a vortex mixer. Dissolution was also facilitated using a spatula resulting in a dark red solution. After approximately 5 minutes an orange red precipitate was noted. Tiny needles exhibiting birefringence were analyzed by XRPD while wet.

Rifaximin (508 mg) was combined with ethanol (1.3 mL) and heated on a hot plate (set point at 70° C.). Water (0.58 mL) was added to the clear solution and heating was continued. A clear brown solution was obtained. The vial was placed in an ice-water bath for approximately 3 hours and then kept at ambient temperature overnight. A portion of the sample was packed into a 1 mm glass capillary and analyzed by XRPD.

Rifaximin (503 mg) was combined with ethanol (1.3 mL) and heated on a hot plate (set point at 70° C.). Water (0.58 mL) was added to the clear solution and heating was continued for approximately 5 minutes. A clear brown solution was obtained. The sample was cooled at 3° C./hour from 70 to 20° C. (instrument set point). After one day, a portion of the sample was packed into a 1 mm glass capillary and analyzed by XRPD.

Rifaximin (402 mg) was combined with ethanol (2.0 mL) and water (0.5 mL). The vial was capped and the slurry placed on a shaker block at ambient temperature. After approximately 5 hours a portion of the sample was packed into a 1 mm glass capillary and analyzed by XRPD.

Rifaximin (0.1004 g) was dissolved in ethanol (340 μL) using a vortex mixer and spatula. A dark red solution was obtained and yielded an orange red precipitate after 5 min. Tiny birefringent needles were submitted wet for XRPD analysis. The sample was analyzed again after 3 months and 7 days of storage at ambient conditions. This sample was on first analysis and Form eta upon re-analysis.

Rifaximin (0.1004 g) was dissolved in ethanol (340 μL) using a vortex mixer and spatula. A dark red solution was obtained and yielded an orange red precipitate after 5 min. Tiny birefringent needles were submitted wet for XRPD analysis. This sample was on first analysis and Form eta upon re-analysis.

The sample was analyzed again after 3 months and 7 days of storage at ambient conditions (a form eta). Rifaximin (0.1004 g) was dissolved in ethanol (340 μL) using a vortex mixer and spatula. A dark red solution was obtained and yielded an orange red precipitate after 5 min. Tiny birefringent needles were submitted wet for XRPD analysis. Form Zeta on first analysis Form eta upon re-analysis. The sample was analyzed again after 3 months and 7 days of storage at ambient conditions.

Methods of Preparation for Rifaximin Form B

Rifaximin (268 mg) was combined with ethanol (1 mL) and water (1 mL) with shaking and sonication. The sample was heated on a hot plate (set temperature 68° C.) resulting in a clear orange solution. Heating was discontinued and the vial allowed to cool to ambient temperature on the hot plate. After 3 days, a small portion of solids and solution were packed in a 1 mm glass capillary was submitted for XRPD analysis.

Rifaximin (268 mg) was combined with ethanol (1 mL) and water (1 mL) with shaking and sonication. The sample was heated on a hot plate (set temperature 68° C.) resulting in a clear orange solution. Heating was discontinued and the vial allowed to cool to ambient temperature on the hot plate. After 3 days, a small portion of solids and solution were packed in a 1 mm glass capillary was submitted for XRPD analysis. Solids were collected from the remaining sample by decantation of solvent. The solids were air dried. Orange blades exhibiting birefringence and extinction were analyzed by XRPD, DSC and TGA.

Rifaximin was slurried on a shaker block at ambient temperature for 2 days. A portion of sample in solution was packed capillary for analysis by XRPD.

Rifaximin (201 mg) was combined dissolved in ethanol (2 mL). The sample was heated on a hot plate (instrument set point 85° C.) resulting in a clear orange solution. Water (2.0 mL) was added and the solution heated for an additional 5 minutes (approximate time). The clear solution was cooled at 5° C./hour from approximately 80-20° C.). After one day large orange blades exhibiting birefringence and extinction were observed and the sample was analyzed wet by XRPD. The sample was also submitted for single crystal structure determination.

Rifaximin was returned from single crystal structure analysis in solution. A small portion of solids and solution were packed in a capillary for XRPD analysis.

Rifaximin (110 mg) was combined with ethanol (4.0 mL) and heated on a hotplate (instrument set point at 80° C.). The clear solution was filtered through a 0.2 um nylon filter. The filtrated was heated (instrument set point at 80° C.) and water (6.0 mL) was added drop wise resulting in a slightly cloudy solution. Heating was discontinued and the sample allowed to remain on the hotplate. A portion of the sample and solvent was placed in a capillary for analysis by XRPD.

Rifaximin (501 mg) was combined with ethanol (1.3 mL) and heated on a hotplate (instrument set point at 75° C.). A clear solution was obtained. Water (0.5 mL) was added and the solution was heated on the hotplate for approximately 5 minutes. (instrument set point at 75° C.). Heating was discontinued and the sample cooled at a rate of 3° C./min from 70-20° C. (instrument set point). After 3 days a small portion of solids and solution were packed into a capillary for XRPD analysis.

Rifaximin (1.1209 g) was spread evenly in a petri dish. The petri dish placed in a jar containing a saturated salt solution in order to maintain a relative humidity of 84%. After 2 days, the solids were removed from the chamber and placed in a vial. The sample was analyzed by XRPD 12 days later.

Form B:

Rifaximin (0.0266 g) was combined with heptane (20.0 mL) with sonication. The sample was slurried at ambient temperature on an orbital shaker (150 rpm). After 3 days the sample noted as completely dried and contained solids exhibiting a morphology similar to broken glass. Birefringence was not observed. The sample was analyzed by XRPD.

Rifaximin (0.0266 g Lot) was combined with heptane (20.0 mL) with sonication. The sample was slurried at ambient temperature on an orbital shaker (150 rpm). After 3 days the sample noted as completely dried and contained solids exhibiting a morphology similar to broken glass. Birefringence was not observed. The sample was analyzed by XRPD.

Rifaximin (0.0288 g) was combined with acetone/water (1/1 v/v, 6.0 mL) with sonication resulting in a clear solution. The solution was filtered through a 0.2 um filter into a clean vial. The vial was left uncapped and solvent allowed to evaporate under ambient conditions. Four days later, orange, birefringent irregular plates were collected by vacuum filtration and dried under reduced pressure for approximately 3 minutes.

Rifaximin (0.0288 g) was combined with acetone/water (1/1 v/v, 6.0 mL) with sonication resulting in a clear solution. The solution was filtered through a 0.2 um filter into a clean vial. The vial was left uncapped and solvent allowed to evaporate under ambient conditions. Four days later, orange, birefringent irregular plates were collected by vacuum filtration and dried under reduced pressure for approximately 3 minutes.

Rifaximin (0.5351 g) was transferred to a vial containing IPA (2.97 mL) and water (30 µL) resulting in a sticky paste. The vial was capped and stored at ambient temperature. Tiny orange particles exhibiting partial birefringence were noted after one day. Solids were collected by vacuum filtration, air dried under reduced pressure for approximately 3 minutes and transferred to a clean vial. The sample was analyzed by XRPD.

Rifaximin (0.5281 g) was transferred to a vial containing IPA (2.91 mL) and water (90 µL) resulting in a sticky paste. The vial was capped and stored at ambient temperature. Tiny orange particles exhibiting partial birefringence were noted after one day. Solids were collected by vacuum filtration, air dried under reduced pressure for approximately 7 minutes and transferred to a clean vial. The sample was analyzed by XRPD.

Instrumental Parameters

All analyses were performed at ambient temperature unless otherwise specified in the parameters.

X-Ray Powder Diffraction (XRPD)

Inel

X-ray powder diffraction analyses were performed using an Inel XRG-3000 X-ray powder diffractometers with Cu Kα radiation. The Inel XRG-3000 diffractometer is equipped with a CPS (Curved Position Sensitive) detector with a 2θ range of 120°. Real time data were collected using Cu-Kα radiation starting at approximately 4°2θ at a resolution of 0.03°2θ. The tube voltage and amperage were set to 40 kV and 30 mA, respectively. The monochromator slit was set at 5 mm by 160 µm. The pattern is displayed from 2.5-40°2θ. Samples were prepared for analysis by packing them into thin-walled glass capillaries. Each capillary was mounted onto a goniometer head that is motorized to permit spinning of the capillary during data acquisition. The samples were analyzed for 5 min. Instrument calibration was performed using a silicon reference standard.

Thermal Analyses

Differential Scanning Calorimetry (DSC)

Differential scanning calorimetry (DSC) was performed using a TA Instruments differential scanning calorimeter 2920. The sample was placed into an aluminum DSC pan, and the weight accurately recorded. The pan was covered with a lid and then crimped or left uncrimped. The sample cell was equilibrated at 25° C. and heated under a nitrogen purge at a rate of 10° C./min, up to a final temperature of 350° C. Indium metal was used as the calibration standard. Reported temperatures are at the transition maxima.

DSC was performed using a TA Instruments Q2000 differential scanning calorimeter. Temperature calibration was performed using NIST traceable indium metal. The sample was placed into an aluminum DSC pan, and the weight was accurately recorded. The pan was covered with a lid, and the lid was crimped. A weighed, crimped aluminum pan was placed on the reference side of the cell. The sample cell was equilibrated at 25° C. and heated under a nitrogen purge at a rate of 10° C./minute, up to a final temperature of 250° C. Reported temperatures are at the transition maxima.

Thermogravimetric (TG) Analyses

Thermogravimetric (TG) analyses were performed using a TA Instruments 2950 thermogravimetric analyzer. Each sample was placed in an aluminum sample pan and inserted into the TG furnace. The furnace was started directly from ambient temperature, then heated under nitrogen at a rate of 10° C./min, up to a final temperature of 350° C. Nickel and Alumel™ were used as the calibration standards.

Dynamic Vapor Sorption (DVS)

Dynamic vapor sorption (DVS) data were collected on a VTI SGA-100 Vapor Sorption Analyzer. NaCl and PVP were used as calibration standards. Samples were not dried prior to analysis. Adsorption and desorption data were collected over a range from 5 to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

Solution 1D 1H NMR Spectroscopy

The solution NMR spectra were acquired with a Varian UNITYINOVA-400 spectrometer. The samples were prepared by dissolving approximately 4-8 mg in acetone-d6 or methanol-d4. The data acquisition parameters are displayed in the first plot of the spectrum in the Data section of this report Infrared Spectroscopy (IR)

IR spectra were acquired on Magna-IR 860® Fourier transform infrared (FT-IR) spectrophotometer (Thermo Nicolet) equipped with an Ever-Glo mid/far IR source, an extended range potassium bromide (KBr) beamsplitter, and a deuterated triglycine sulfate (DTGS) detector. Wavelength verification was performed using NIST SRM 1921b (polystyrene). An attenuated total reflectance (ATR) accessory (Thunderdome™, Thermo Spectra-Tech), with a germanium (Ge) crystal was used for data acquisition. Each spectrum represents 256 co-added scans collected at a spectral resolution of 4 cm-1. A background data set was acquired with a clean Ge crystal. A Log 1/R (R=reflectance) spectrum was obtained by taking a ratio of these two data sets against each other.

Hot Stage Microscopy

Hot stage microscopy was performed using a Linkam hot stage (model FTIR 600) mounted on a Leica DM LP microscope equipped with a SPOT Insight™ color digital camera. Temperature calibrations were performed using USP melting point standards. The camera is white balanced. Samples were placed on a cover glass, and a second cover glass was placed on top of the sample. As the stage was heated, each sample was visually observed using a 20×0.40 N.A. objective with crossed polarizers or without top polarizer, and a first order red compensator. Images were captured using SPOT Advance software (v. 4.5.9).

XRPD Data and Indexing Results

The Topas refinement method used to determine the DP value for each measured XRPD data file.

Topas was operated in a mixture plus unit cell refinement mode rather than the usual Rietveld mode. In this limited refinement mode, the initial refinement pass was used to estimate the phase composition represent by the data file under analysis. Many of the measured XRPD data sets represent mixtures of various rifaximin phases which were removed to allow analysis of the pure phases.

For the remaining data sets judged to represent pure phases, the unit cell parameters of the corresponding phase model in Topas were allowed to vary along with an angular offset and sample displacement parameter. The unit cell parameters resulting from the best fit to the measured data were used to determine the DP (dimensionless product) value corresponding to that data set.

Topas Phase Models

Topas is a Rietveld refinement package that has XRPD pattern fitting capabilities. Each of the crystalline phases (forms) that Topas can model must first be loaded as an effective crystal structure using CIF files. The effective crystal structure for each crystalline form was determined using a measured reference pattern for that phase and an approximate starting structure. For the forms with single crystal structures, the CIF files corresponding to those crystal structures were used as the starting structures (usually the single crystal structures are determined at low temperatures, which require unit cell refinement to correctly describe a powder pattern measured under ambient conditions). For forms without known crystal structures, an approximate starting structure was derived from the closest matching known structure and an index solution to the powder pattern. The indexing was performed using Dicvol v4.0. Some XRPD reference patterns did not yield an index solution due to the lack of well defined free standing diffraction peaks. For these patterns, extensive refinement of the known crystal structures was required to achieve a reasonable effective crystal structure.

The effective crystal structure is not a solution to the actual crystal structure of a form but is a structural model that provides a good fit to the measured XRPD reference pattern for that form.

Topas Mixture Refinement

Many of the XRPD data sets initially grouped as potentially representing pure phase material actually represented mixtures. To isolate only the pure phase data sets for subsequent DP analysis, Topas was initially configured with an ensemble of effective crystal structures representing the potential mixtures. During the first refinement pass, only the concentration of the individual phases (and some general scale actors) were allowed to refine. If the resulting best fit to the measured data gave a primary phase contribution of <70%, the data was rejected from the pure phase cluster and flagged as potentially representing a mixture.

Topas Unit Cell Refinement

XRPD data sets representing pure phase material were modeled in Topas using unit cell refinement of the corresponding effective crystal structure. Along with the unit cell parameters (a, b, c, alpha, beta, gamma), an instrument offset parameter and sample displacement parameter were refined. The resulting best fit unit cell was exported as an INP file.

Characteristic peaks of Forms ι, ι-dry, ζ, and B that differentiate one crystalline polymorph from another crystalline form are shown below in Table _. Characteristic peaks are determined by evaluating which peaks are present in one crystalline form of a compound against all other known crystalline form of that compound to within ±0.15°2θ. Some crystalline forms do not exhibit a characteristic peak, however, when combined with other peak(s), the set of peaks differentiate the crystalline form from other crystalline forms.

Shown below are Tables with peak lists for forms described herein. Fewer than the described peaks, as listed above are identifying for the forms. A selection of peaks, from between 2-10 peaks could be identifying for a particular form.

TABLE 1

Characteristic XRPD peak and peak sets of each crystalline form of rifaximin

| Form Iota dry' | Form Iota dry' | Form Iota | Form Zeta | Form B |
|---|---|---|---|---|
| 6.045 | 6.165 | 5.495 | 4.69 ± 0.15 | 5.24 ± 0.15 |
| 7.905 | 7.925 | 5.885 | 7.63 ± 0.15 | 6.84 ± 0.15 |
| 8.925 | 8.895 | 7.865 | 12.52 ± 0.15 | 7.74 ± 0.15 |
| 9.495 | 9.555 | 9.035 | 13.87 ± 0.15 | 8.71 ± 0.15 |
| 12.765 | 12.805 | 12.665 | | 10.16 ± 0.15 |
| 14.145 | 14.255 | 13.895 | | 12.21 ± 0.15 |

TABLE 2

Peak List for Iota dry

| Row | °2θ | Relative Intensity (%) |
|---|---|---|
| 1 | 6.04 ± 0.15 | 80 |
| 2 | 7.90 ± 0.15 | 100 |
| 3 | 8.92 ± 0.15 | 59 |
| 4 | 9.49 ± 0.15 | 54 |
| 5 | 12.76 ± 0.15 | 61 |
| 6 | 14.14 ± 0.15 | 53 | a. Unique peak clusters at +/−0.15°2θ matching window against all phases except iota dry (prime)

b. Doublets 1) 1+3 and 2) 3+6 c. Triplets—none d. Iota dry is distinguishable from Iota's' but requires a narrower error window of +/−0.1

TABLE 3

Peak List for Iota dry'

| Row | °2θ | Relative Intensity (%) |
|---|---|---|
| 1 | 6.16 ± 0.15 | 99.6 |
| 2 | 7.92 ± 0.15 | 100 |
| 3 | 8.89 ± 0.15 | 52.2 |
| 4 | 9.55 ± 0.15 | 57.2 |
| 5 | 12.80 ± 0.15 | 56.2 |
| 6 | 14.25 ± 0.15 | 57.3 | a. Unique peak clusters at +/−0.15°2θ matching window against all phases except iota dry b. Doublets—none c. Triplets 1) 1+2+6 and 2) 1+3+6 and 3) 2+4+6 d. Iota's dry' is distinguishable from Iota's dry with a +/− error windrow.

TABLE 4

Peak List for Iota

| Row | °2θ | Relative Intensity (%) |
|---|---|---|
| 1 | 5.49 ± 0.15 | 70.22 |
| 2 | 5.88 ± 0.15 | 67.46 |
| 3 | 7.86 ± 0.15 | 100 |
| 4 | 9.03 ± 0.15 | 57.61 |
| 4 | 12.66 ± 0.15 | 62.17 |
| 6 | 13.89 ± 0.15 | 54.4 | a. Unique peak clusters at +/−0.15°2θ matching window against all phases b. Doublets—none c. Triplets 1) 1+2+4 and 2) 1+2+6 and 3) 2+4+5 and 4) 2+4+6

TABLE 5

Peak List for Zeta

| Row | °2θ | Relative Intensity (%) |
|---|---|---|
| 1 | 4.69 | 100 |
| 2 | 7.63 | 63.48 |
| 3 | 12.52 | 24.68 |
| 4 | 13.87 | 24.81 | a. Unique peak clusters at +/−0.15°2θ matching window against all phases b. Doublets 1) 1+2 c. Triplets 1) 2+3+4 d. Matching against patented forms (α, β, δ, γ, ε)—no overlap

TABLE 6

Peak List for Form B

| Row | °2θ | Relative Intensity (%) |
|---|---|---|
| 1 | 5.24 | 100.0 |
| 2 | 6.84 | 79.9 |
| 3 | 7.74 | 96.9 |
| 4 | 8.71 | 39.4 |
| 5 | 10.16 | 73.2 |
| 6 | 12.21 | 38.6 | a. Unique peak clusters at +/−0.15°2θ matching window against all phases b. Doublets 1) 1+5 c. Triplets 1) 2+3+4 and 2) 1+3+4 and 3) 1+4+6 and 4) 2+3+4 and 5) 2+3+5 and 6) 2+4+5 and 7) 4+5+6 d. Matching against patented forms (α, β, δ, γ, ε)—no overlap

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A polymorphic Form B of rifaximin, wherein the polymorph exhibits an X-ray powder diffraction pattern having characteristic peaks expressed in degrees 2θ (+/−0.20 degree θ) at 5.24, 6.84, 7.74, 8.71, 10.16, and 12.21.

2. The polymorph Form B of claim 1, wherein the polymorph comprises from between about 50 to about 100% pure polymorphous form before or after formulation.

3. The polymorph Form B of claim 1, wherein the polymorph comprises from between about 75 to about 100% pure polymorphous forms before or after formulation.

4. A pharmaceutical dosage form comprising the polymorphic Form B of claim 1.

* * * * *